US012751777B1

(12) United States Patent
Kam et al.

(10) Patent No.: US 12,751,777 B1
(45) Date of Patent: Oct. 6, 2026

(54) SYSTEM, METHOD, AND APPARATUS FOR TRACKING AND LABELING SURGERY TOOLS

(71) Applicant: Digital Surgery Systems, Inc., Goleta, CA (US)

(72) Inventors: Kyle Kam, San Mateo, CA (US); Mannat Rana, Phoenix, AZ (US)

(73) Assignee: Digital Surgery Systems, Inc., Goleta, CA (US)

( * ) Notice: Subject to any disclaimer, the term of this patent is extended or adjusted under 35 U.S.C. 154(b) by 0 days.

(21) Appl. No.: 19/234,164

(22) Filed: Jun. 10, 2025

(51) Int. Cl.
*H04N 23/68* (2023.01)
*A61B 34/20* (2016.01)
*G06T 7/246* (2017.01)
*G06T 7/277* (2017.01)
*G06T 7/73* (2017.01)
*G16H 30/40* (2018.01)
*A61B 34/10* (2016.01)

(52) U.S. Cl.
CPC .............. *A61B 34/20* (2016.02); *G06T 7/248* (2017.01); *G06T 7/277* (2017.01); *G06T 7/74* (2017.01); *G16H 30/40* (2018.01); *H04N 23/6811* (2023.01); *H04N 23/683* (2023.01); *A61B 2034/107* (2016.02); *A61B 2034/2055* (2016.02); *A61B 2034/2065* (2016.02); *G06T 2207/10016* (2013.01); *G06T 2207/10056* (2013.01); *G06T 2207/20084* (2013.01); *G06T 2207/30004* (2013.01); *G06T 2207/30241* (2013.01)

(58) Field of Classification Search
USPC .............................................................. 348/79
See application file for complete search history.

(56) References Cited

U.S. PATENT DOCUMENTS

| | | | | |
|---|---|---|---|---|
| 10,129,658 | B2 * | 11/2018 | Rubinstein | G01H 9/002 |
| 2018/0268237 | A1 * | 9/2018 | Stanimirovic | G06T 7/248 |
| 2019/0122378 | A1 * | 4/2019 | Aswin | G06V 20/647 |

* cited by examiner

*Primary Examiner* — Nigar Chowdhury
(74) *Attorney, Agent, or Firm* — Rimon PC

(57) ABSTRACT

The present invention relates to surgical image processing and update by a computing device. The method disclosed herein uses a deep learning model to detect distal ends of tools in an image from a microscope and processes the image to output detections that are optionally displayed around the distal ends of the tools. The method disclosed herein also uses Kalman filters and camera motion compensation calculations to process the image and predict the locations and sizes of the bounding boxes around the distal ends of the tools. The two processes work parallelly, with the Kalman filters and camera motion compensation calculations working at a higher rate than the deep learning model, thereby allowing an increased update rate of detections while not significantly increasing computing workload.

20 Claims, 9 Drawing Sheets

SYSTEM, METHOD, AND APPARATUS FOR TRACKING AND LABELING SURGERY TOOLS

BACKGROUND

Surgery is a medical procedure involving insertion of various tools into a living organism body. Surgeons are craftspeople who rely strongly on their hands and/or feet to achieve their objectives during surgery. During surgical and microsurgical procedures for which a microscope is used, control of the surgical microscope, particularly its position and orientation, often involves physical input from the surgeon's hands and/or feet. This reliance on the hands and/or feet can cause unnecessary interruptions in the surgery, place the surgeon off-balance in the case of foot pedal use, increase procedure time, or otherwise negatively impact patient outcomes.

Surgeon hand-based systems may include hand controls, as the hands are often the primary tools for controlling various features on existing surgical microscopes. However, hand controls may often require the surgeon to remove one or more of their hands from their primary task of controlling their surgical tools. Thus, hand controls may negatively impact surgical time and may impair the surgeon's focus and flow.

Another system for assisting surgeons involves foot control. Legacy foot pedals may include foot-controlled buttons for performing simple functions and a joystick for motion control. Many surgeons are averse to using a foot pedal for microscope control during sensitive surgical maneuvers because of the high level of control required by their hands for controlling the surgical tools. Using the foot pedal can cause the surgeon to shift their body weight on the foot that is not controlling the foot pedal, and this shift can put the surgeon off-balance. Additionally, there is often a scarcity of space around the surgeon's feet owing to other devices offering foot pedals. These other devices that also offer foot pedals may remain in place for the whole procedure regardless of whether these other devices are actually in use.

Another system for assisting surgeons involves voice controls. Voice control can work well for simple commands (e.g., "increase light" or "zoom in") that do not necessarily involve motion. However, having voice control for more extensive or motion-based commands, such as controlling the motion of a robot during surgery, may not be advised due to the greatly increased specificity required, as well as risk of patient injury.

Another system for assisting surgeons involves the use of navigation or tracker tools. For example, SYNAPTIVE'S MODUS V may provide microscopic motion and optics control functionality. However, such features are costly as they involve bulky navigation targets added to the tools. The targets may either add on to existing tools or may be built into a proprietary costly toolset that may need to be purchased by the user. Add-on targets may involve an extra registration step at procedure time to inform the system of tool geometry relative to the add-on tracker target. In such cases, the tracker target may need to be kept in view of the navigation camera, which can become onerous or may cause intermittent disruptions due to objects blocking the line of sight between the navigation camera and the tool-mounted target(s).

Output of tool tracking methods and devices in the form of images displayed on a screen is subject to image processing speed and capacity of the computer wherein the images are processed. For tool tracking methods using a deep learning network, processing rate is dependent upon computing power of a processor, and in many cases latency of the output affects update rate, resulting in a track that is not smooth, i.e., with a low update rate, such that tracks shown to user are perceived as less fluid than a motion video.

There exists a demand for digitally tracking surgical tools of similar appearances and sizes during a surgery with an output track providing identification and display of precise locations of multiple tools and conducive for viewing at an update rate perceived as real motion while using less computer processing power. The present invention addresses this and other related needs in the art.

SUMMARY

According to frequently included embodiments, there is provided a method of processing video images of a surgical site, the method comprises:

- receiving, in real-time, by a computing device having a processor, image data of an image in a surgical video stream comprising a plurality of images captured by a camera of a digital surgical microscope, wherein the surgical video stream shows at least one tool;
- determining the order of receipt of the image;
- for the first and every $[(n+1)\times i]^{th}$ image:
  - applying the image data from an image in the surgical video stream to a first trained neural network model to determine a location for a bounding box around a distal end point of each of the at least one tool;
  - generating processed image data comprising a bounding box around the distal end point of the at least one tool;
  - applying the processed image data to a second trained neural network model to track the distal end point of each of the at least one tool;
  - initializing a trajectory for each bounding box and setting up a Kalman filter for each trajectory;
  - calculating camera motion compensation for the image data received as compared to the image data of an immediate previous image in the surgical video stream;
  - predicting parameters of the bounding box of each of the at least one tool using the Kalman filter associated with the trajectory;
  - correcting the prediction of the Kalman filter using the calculated camera motion compensation;
  - matching the bounding box as generated in the processed image data and the bounding box as predicted by the Kalman filter;
  - marking a trajectory as present if a bounding box as predicted by the Kalman filter is matched with a bounding box in the processed image data and updating the Kalman filter with the processed image data concerning the matched bounding box;
  - marking a trajectory as lost if a bounding box as predicted by the Kalman filter is not matched with a bounding box in the processed image data;
- sending the present trajectories and the initialized trajectories to a user interface module; and
  - displaying the trajectories at a display using the user interface module;
- for every image not the first or $[(n+1)\times i]^{th}$ image:
  - calculating camera motion compensation for the image data received as compared to the image data of the immediate previous image;

predicting the next parameters of the bounding box of each of the at least one tool using the Kalman filter and the calculated camera motion compensation; and displaying an image using image data from the prediction at a display using the user interface module, wherein n is a predetermined integer and i starts at 1 and increases by 1 each time, wherein the processed image data comprises a location and a size of the bounding box, a label, and the bounding box confidence, wherein the parameters of the bounding box comprise a location, a size, a velocity, and a velocity of size change of the bounding box, and wherein the trajectory is a collection of digital image data concerning a bounding box collected over time.

According to often included embodiments, there is provided a method as above, wherein the at least one tool is a scalpel, a knife, a pair of forceps, a needle, a retractor, a rongeur, a hemostats trocar, a Yankauer, a knife handle with a blade, a knife handle without a blade, a bonnet, a pair of straight hemostats, a pair of curved hemostats, an iris scissor, a Pennfield freer, a ball tip probe, a nerve hook, a curet, a posterior cobb elevator, or an osteotome.

According to frequently included embodiments, there is provided a method as above, wherein applying the image data to the first trained neural network model comprises:

generating a first input feature vector based on the image data; and applying the first input feature vector to the first trained neural network model to generate a first output feature vector, wherein the first output feature vector indicates the location, the size, the label, the velocity, and the velocity of the bounding box size change of the bounding box of each of the at least one tool.

According to often included embodiments, there is provided a method as above, wherein applying the processed image data to the second trained neural network model comprises:

generating a second input feature vector based on the processed image data; and applying the second input feature vector to the second trained neural network model to generate a second output feature vector, wherein the second output feature vector indicates the location for the distal end of each of the at least one tool.

According to frequently included embodiments, there is provided a method as above, wherein calculating camera motion compensation comprises using Oriented FAST Rotated BRIEF technique or sparse optical flow technique.

According to often included embodiments, there is provided a method as above, wherein updating the Kalman filter comprises updating the location, label, and size of the bounding box and updating estimated current state variables using weighted averages.

According to frequently included embodiments, there is provided a method as above, wherein the value of n is chosen by a user.

According to often included embodiments, there is provided a method as above, wherein n is 0.

According to frequently included embodiments, there is provided a method as above, the method further comprises, prior to applying the image data to the first trained neural network model:

receiving a plurality of reference image data of a reference surgical video, wherein each reference image data represents a respective image frame showing a plurality of tools;

generating, for each of the plurality of reference image data, a reference input feature vector indicating relevant features of the reference image data, and a reference output feature vector indicating a label, a location, a size; and training, by associating each reference input feature vector with its respective reference output feature vector, a neural network to form the first trained neural network model.

According to often included embodiments, there is provided a method as above, further comprising:

identifying, by the computing device, based on a previously received image data of the surgical video stream, a displacement of a feature in the surgical video stream beyond a threshold distance; and choosing one tool among the at least one tool and causing the digital microscope to track the distal end of the chosen one tool, wherein the steps of claim 1 are conducted responsive to the identified displacement.

According to frequently included embodiments, there is provided a method as above, further comprising:

setting a value reflecting how many times a trajectory is marked as lost before removing a trajectory;

counting the times a trajectory is marked as lost; and removing the trajectory when the times have reached the value, wherein the value is an integer.

According to often included embodiments, there is provided a system for processing video images of a surgical site in real-time, the system comprises a digital surgical microscope (DSM) comprising a DSM camera; a processor; and a memory device storing computer-executable instructions that, when executed by the processor, causes the processor to:

receive, in real-time, by a computing device having a processor, image data of an image in a surgical video stream captured by a camera of the digital surgical microscope, wherein the surgical video stream shows at least one tool;

determine the order of receipt of the image;

for the first and every $[(n+1)\times i]^{th}$ image:

apply the image data to a first trained neural network model to determine a location for a bounding box around a distal end point of each of the at least one tool;

generate processed image data comprising a bounding box around the distal end of the at least one tool;

apply the processed image data to a second trained neural network model to track the distal end point of each of the at least one tool;

initialize a trajectory for each bounding box and setting up a Kalman filter for each trajectory;

calculate camera motion compensation for the image data received as compared to the image data of an immediate previous image;

predict parameters of the bounding box of each of the at least one tool using the Kalman filter associated with the trajectory;

correct the prediction of the Kalman filter using the calculated camera motion compensation;

match the bounding box as generated in the processed image data and the bounding box as predicted by the Kalman filter;

mark a trajectory as present if a bounding box as predicted by the Kalman filter is matched with a bounding box in the processed image data and updating the Kalman filter with the processed image data concerning the matched bounding box;

mark a trajectory as lost if a bounding box as predicted by the Kalman filter is not matched with a bounding box in the processed image data;

send the present trajectories and the initialized trajectories to a user interface module; and display the trajectories at a display using the user interface module;

for every image not the first or $[(n+1)\times i]^{th}$ image:

calculate camera motion compensation for the image data received as compared to the image data of the immediate previous image;

predict the next parameters of the bounding box of each of the at least one tool using a Kalman filter and the calculated camera motion compensation;

send the predicted image data to the user interface; and display the predicted image at a display using the user interface module, wherein n is a predetermined integer and i starts at 1 and increases by 1 each time, wherein the processed image data comprises a location and a size of the bounding box, a label, and the bounding box confidence, wherein the parameters of the bounding box comprise a location, a size, a velocity, and a velocity of size change of the bounding box, and wherein the trajectory is a collection of digital image data concerning a bounding box collected over time.

According to frequently included embodiments, there is provided a system as above, wherein the instructions, when executed, further causes the processor to:

generate a first input feature vector based on the image data; and apply the first input feature vector to the first trained neural network model to generate a first output feature vector, wherein the first output feature vector indicates the location for the bounding box around each of the at least one tool.

According to often included embodiments, there is provided a system as above, wherein the instructions, when executed, further causes the processor to apply the processed image data to the second trained neural network model, wherein applying the processed image data to the second trained neural network model comprises:

generating a second input feature vector based on the processed image data; and applying the second input feature vector to the second trained neural network model to generate a second output feature vector, wherein the second output feature vector indicates the location for the distal end of each of the at least one tool.

According to frequently included embodiments, there is provided a system as above, wherein calculating camera motion compensation comprises using Oriented FAST Rotated BRIEF technique or sparse optical flow technique.

According to often included embodiments, there is provided a system as above, wherein updating the Kalman filter comprises updating the location, label, and size of the bounding box and updating estimated current state variables using weighted averages.

According to frequently included embodiments, there is provided a system as above, wherein the value of n is chosen by a user.

According to often included embodiments, there is provided a system as above, wherein n is 0.

According to frequently included embodiments, there is provided a system as above, wherein the instructions, when executed, further causes the processor to, prior to applying the image data to the first trained neural network model:

receive a plurality of reference image data of a reference surgical video, wherein each reference image data represents a respective image frame showing a plurality of tools;

generate, for each of the plurality of reference image data, a reference input feature vector indicating relevant features of the reference image data, and a reference output feature vector indicating a location for a bounding box around each of the plurality of tools; and train, by associating each reference input feature vector with its respective reference output feature vector, a neural network to form the first trained neural network model.

According to often included embodiments, there is provided a system as above, wherein the instructions, when executed, further causes the processor to:

set a value reflecting how many times a trajectory is marked as lost before removing a trajectory;

count the times a trajectory is marked as lost; and remove the trajectory when the times have reached the value, wherein the value is an integer.

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only.

DETAILED DESCRIPTION

For clarity of disclosure, and not by way of limitation, the detailed description of the invention is divided into the subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, the term "track," when used as a noun, means a series of digital images shown in successive order in a medium perceivable by a human eye.

As used herein, the term "trajectory" means a collection of digital image data concerning a bounding box placed over a surgical tool tip collected over time.

In embodiments disclosed herein, a method to label and track surgical tools in a video display is provided. An external microscope camera records a video stream at a surgery site, and the video stream is displayed on a computer screen. Computer vision techniques are used to detect and track different tools as they move around in the surgical site, such that the same tool can be continuously labeled and tracked on the video display in real time.

Figure 1:
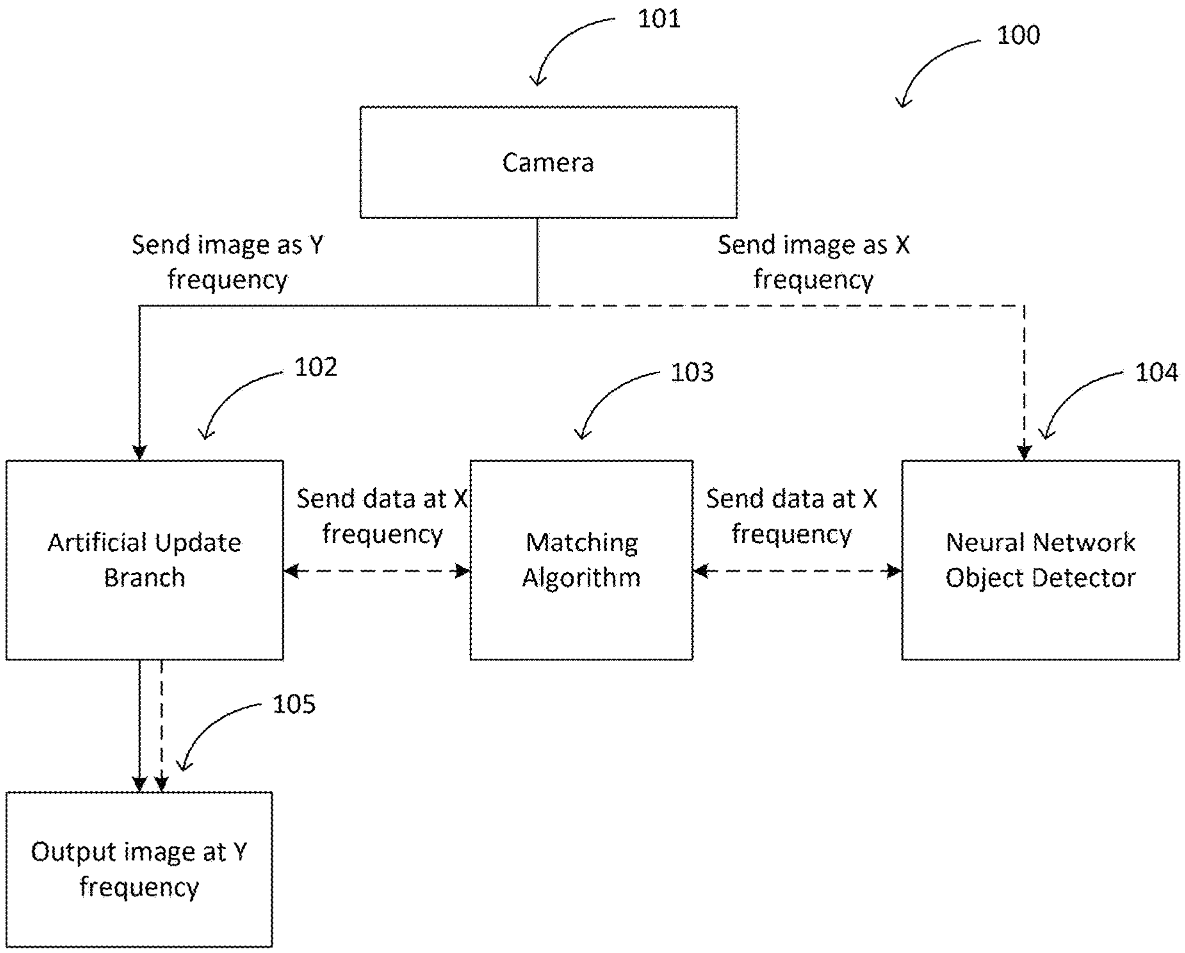
FIG. 1 depicts a diagram of an image processing software to provide tool labeling and tracking for multiple tools in an image of a surgical site according to embodiments herein.

FIG. 1 illustrates the operation of a method according to embodiments herein. An external microscope camera 101 records a video in the nature of a series of images taken at rapid succession. The camera 101 sends images at X frequency to a neural network object detector software branch 104 and at Y frequency to an image processing image prediction software branch 102, with Y larger than X. When an image is sent to both software branches, the image is processed by both branches parallel with a matching algorithm at the end. The matching algorithm matches detection from the neural network object detector with prediction from the artificial update branch, provides updated system parameters to the image prediction software branch, initializes images of tools detected but not predicted, removes images of tools predicted but not detected, and provides images with detected tools for outputting. When an image is sent only to the image prediction software branch, the image prediction software processes the image alone by predicting locations of tools in an image and outputting the predicted image. Working together, the neural network object detector and the image prediction software provide an update rate at Y frequency. On a computing article with a computing processor unit, images are processed in a neural network object detector at a frequency of, for example, 15 frames per second (FPS), this represents X frequency. An image prediction software branch processes images at the frequency of, for example, 60 FPS, this represents Y frequency. The output of processed images at a user interface (e.g., a computer screen) is at the frequency of 60 FPS. Such frequencies are provided without excessive strain on computing resources that would otherwise require additional processing power.

Systems and methods are presented herein for tracking markerless tools. To avoid the need to mark tools, a markerless technique is implemented, as will be discussed. The markerless technique may rely on one or more machine learning networks which may be variously referred to as: artificial neural networks; deep learning; deep learning models; deep learning networks; deep learning neural networks; deep neural network (DNN), neural network (NN). In one embodiment, a specialized version of a DNN, e.g., a convolutional neural network (CNN) may be used, especially as CNN is suited for image processing.

Training Model for the First Neural Network

Figure 2:
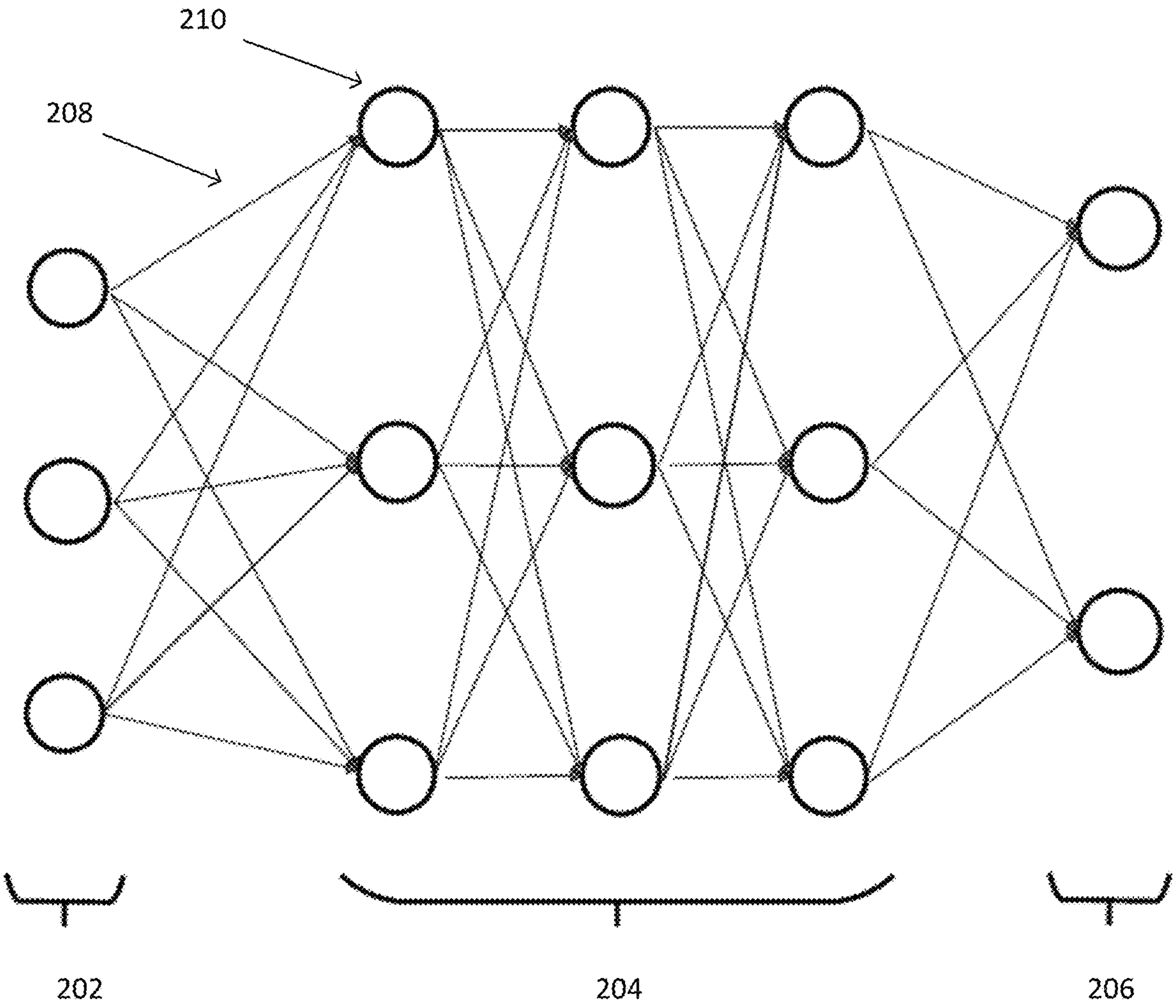
FIG. 2 depicts a diagram of an example deep learning model used for tracking a tool via a digital surgical microscope.

FIG. 2 shows a diagram of an exemplary deep learning model used for tracking a tool via a digital surgical microscope, according to an example embodiment of the present disclosure. As shown in FIG. 2, a node 210, referred to in DNN as a neuron 210, may be a basic building block of a DNN. One or more neurons may be grouped into a layer (e.g., layers 202, 204, and 206). A deep learning network can typically have an input layer 202, one or more hidden layers 204, and an output layer 206. Within each layer, there may be one or more connected neurons, and neurons may connect across layers. Typically, most neurons may be connected to many other neurons. Inputs and outputs of neurons (e.g., the network as a whole) may be represented numerically. The neurons may implement a set of mathematical functions on the numeric input(s) to create one or more numeric outputs. The mathematical functions may include, for example, a multiplication by some weight(s) 208, an addition of some bias(es), and an application of some typically nonlinear processing via an activation function. A node containing a combination of the above-described functions may be referred to as a perceptron. The mathematical function (e.g., activation function) may depend on a node from one layer to a node in the next layer and may rely on a weight 208 assigned between each node. The weights 208 may be initialized and may be subsequently adjusted through an iterative process (e.g., backpropagation). The weights, biases and other configuration values used in the network may be determined during a training phase. In some embodiments, the neural network or networks may be trained via supervised learning. Supervised learning may take as an input a (typically very large) set of labeled information. A labeled information may comprise information where a human processes an input, for example, an image from the digital surgical microscope, and writes out a label in the form of a computer-readable file comprising numeric information.

The training of the machine learning model (e.g., neural network) can happen offline before runtime. The trained model may be output as a model architecture along with weights, biases, and/or other configuration parameters developed by the training phase. As used herein, an inference may refer to a runtime use of the trained model with its configuration parameters in place. The input may be put into the input layer of the model. The output or outputs can thus be inferred from that input. As used herein, a prediction may also refer to the output of the model. A probability may often accompany the output(s) and may describe the likelihood that the detected object and other output parameters are actually correct.

Computation during runtime may be performed via processor modules connected informationally to and located outside, or located inside, the digital surgical microscope. The processor modules may be referred to herein as inference modules and may operate on a variety of hardware, including, but not limited to: a generic central processing unit (CPU) processor (e.g., INTEL® CORE 17-9700K); a generic graphics processing unit (GPU) (e.g., NVIDIA® GTX 1070, RTX 4090); a specialized GPU tailored to perform inference (e.g., a "tensor core" present in NVIDIA®'S VOLTA and TURING architectures); a dedicated inference device (e.g., INTEL® NEURAL COMPUTE STICK 2) or cloud-based solutions on the Internet (e.g., AMAZON® WEB SERVICES).

As many images of the video stream as possible, single image frames captured by the digital surgical microscope may be sent to the inference module for processing. To improve performance, preprocessing steps can occur to reduce the amount of processing power required. For example, the stereoscopic image in some embodiments may be pruned to just one view, for example, to just the left eye. Also or alternatively, the stereoscopic image may be reduced in resolution. For example, the stereoscopic image may be scaled down in its width and its height, e.g., so that it is ¼ the original width and ¼ the original height, e.g., using an OpenCV computer vision function.

Neural networks may be used in various modes. For example, as will be described in FIGS. 3 & 5, a first stage neural network may be trained and applied to generate a bounding box around a tool. A heuristic method may be used to determine the distal end of a tool (e.g., suction cannula, knife, etc.). Furthermore, as will be described in FIGS. 4 & 5, a second stage deep learning, and/or a differently trained first stage neural network may be used to determine distal ends of a tool more deterministically per monoscopic image, e.g., by using training images with the distal tip bounding box labeled. A stereoscopic (or other multi-camera, also known as multi-view) determination of bounding box and distal end can allow the determination of distal end locations in a coordinate space of a camera. Further calibration and registration can allow the transformation to other desirable spaces, e.g., microscope space and patient data space.

Figure 3:
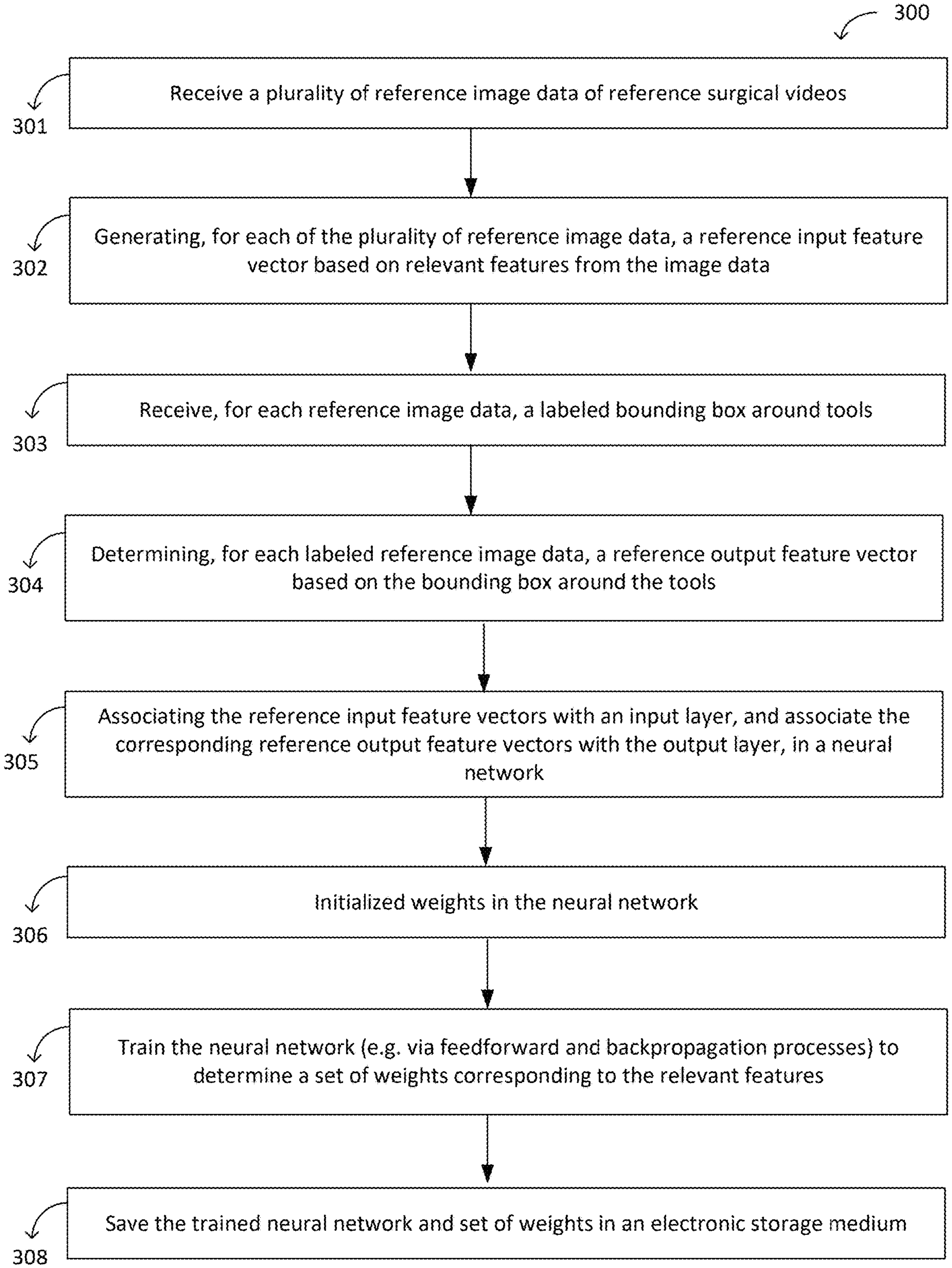
FIG. 3 depicts a flow diagram of a method of training a deep learning model for generating a bounding box around a tool.

FIG. 3 shows a flow diagram of a method of training a deep learning model for generating a bounding box around a tool, according to an example embodiment of the present disclosure. One or more steps of method 300 may be performed by a computing device having a processor. For example, the digital surgical microscope may comprise or may be associated with a computing device. Processor modules may be connected informationally to and located outside, or located inside, the digital surgical microscope. The processor may execute one or more steps or methods discussed herein (e.g., in FIGS. 3-5) based on computer-executable instructions stored in a memory device of the computing device.

Figure 4:
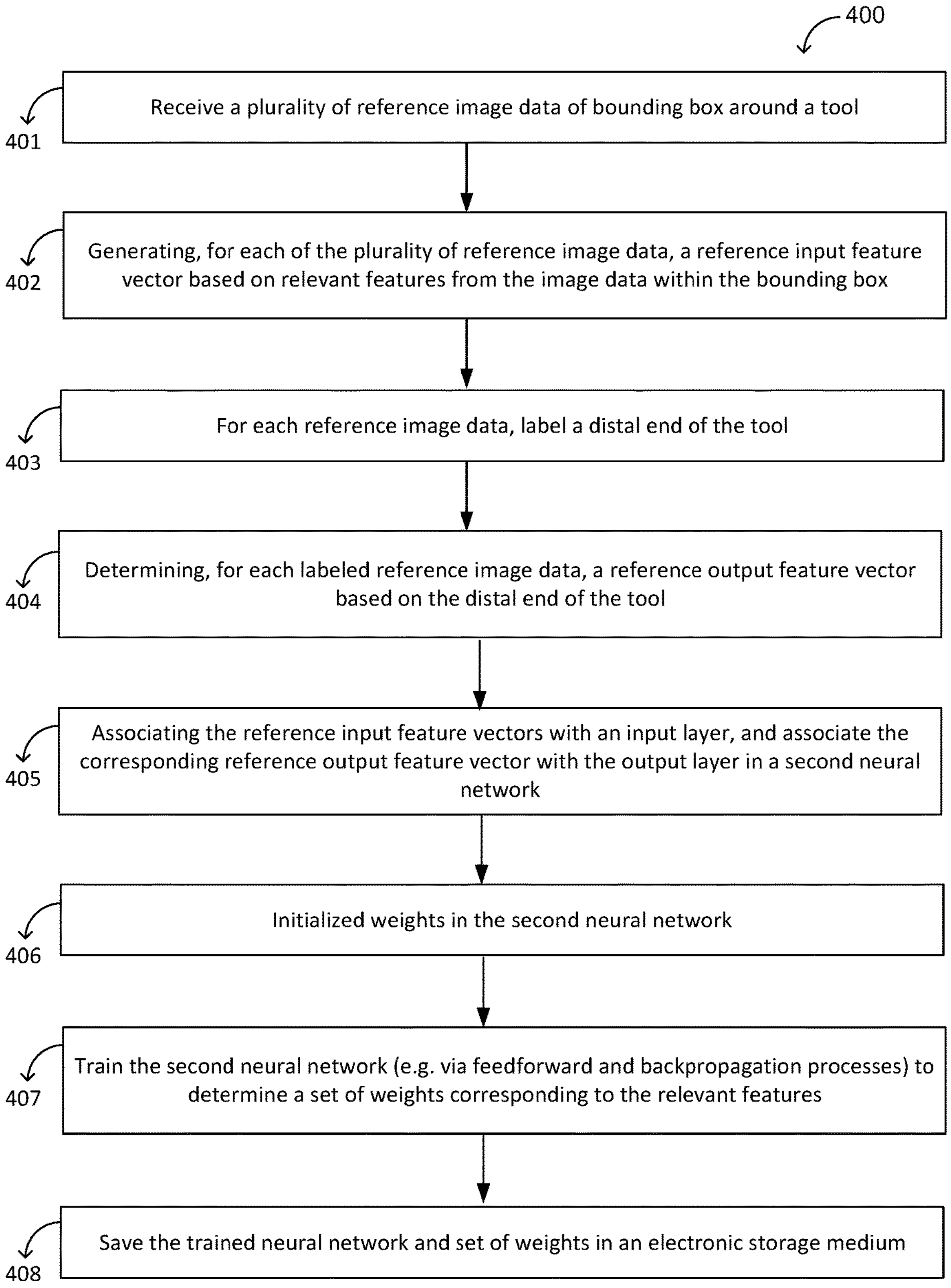
FIG. 4 depicts a flow diagram of a method of training a deep learning model for detecting a distal end of a tool from image data.
Figure 5:
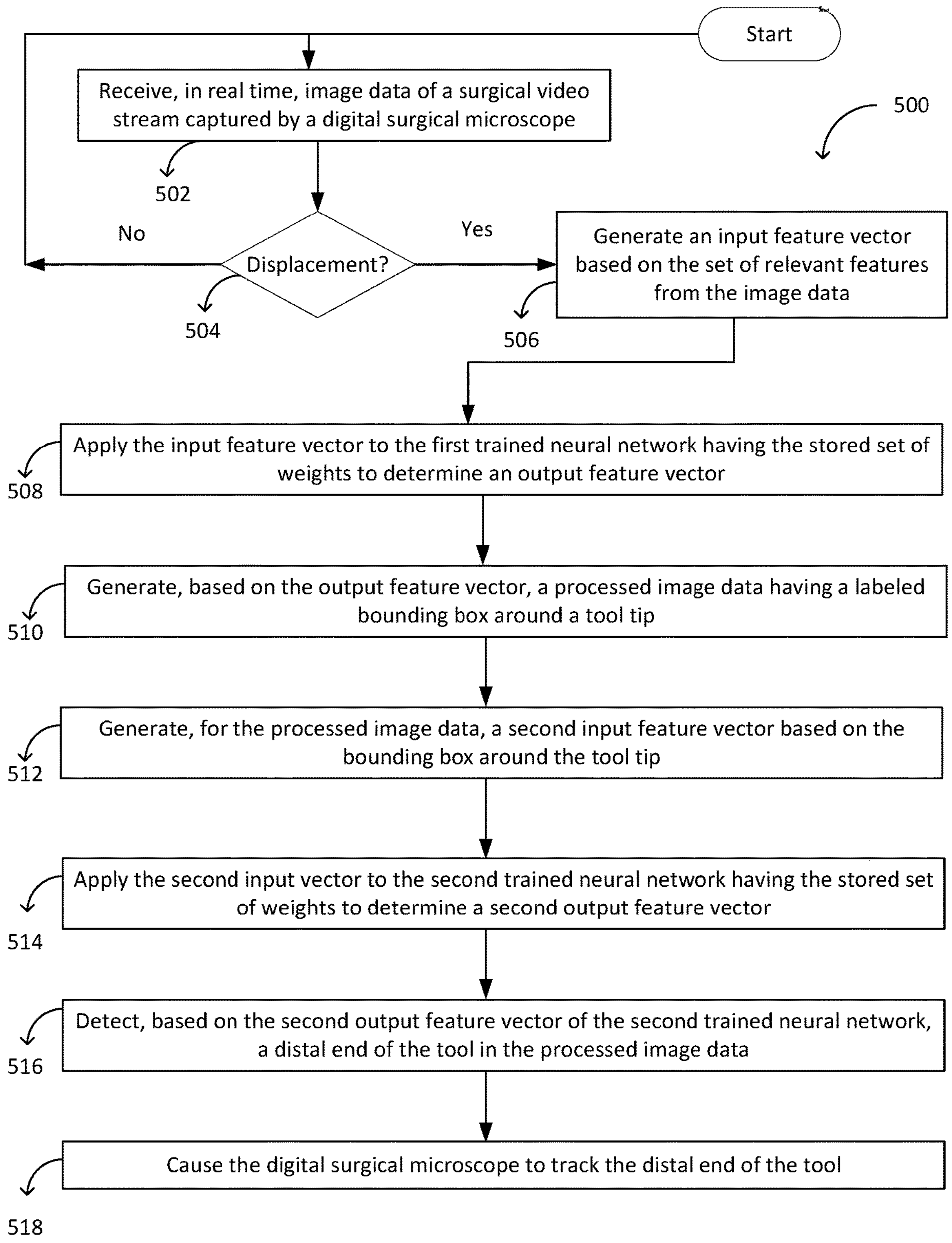
FIG. 5 depicts a flow diagram of a method of applying deep learning models for detecting and tracking a tool from image data in real-time.

In some embodiments, the reference image data and/or the reference surgical videos may be obtained from the surgical site, surgery room, or medical facility used for surgery in which the trained machine learning models are to be eventually applied, in real-time, for the automated tracking of tools (e.g., in method 500 of FIG. 5). Also or alternatively, the reference image data and/or the reference surgical videos may be obtained from images or surgical videos of the surgeon operating and/or the surgeon's tool employed during the surgery in which the trained machine learning models are to be eventually applied, in real-time, for the automated tracking of tools (e.g., in method 500 of FIG. 5). By training neural network models using training data directly obtained from images, settings, and/or tools on which the trained neural networks are to be applied, the neural network models may be more specific, and therefore more effective and accurate for their end goals (e.g., the first neural network model for determining a bounding box around a tool as explained in FIG. 3), and the second neural network model for detecting a distal end of the tool (e.g., as will be explained in FIG. 4).

At step 302, the computing device may generate, for each of the plurality of reference image data, an input feature vector based on relevant features from the image data. For example, relevant features may include, but are not limited to, the color of an individual pixel of the image data, a contrast of an individual pixel in relation to neighboring pixels, a brightness of an individual pixel, a degree of similarity with a neighboring pixel, a curvature. In some embodiments, for example, where a convolutional neural network model is to be implemented, the feature vectors may be automatically determined based on the convolved image data. In such embodiments, the relevant features may not necessarily be features that a human could relate to.

A supervised machine learning model may involve learning from training data, e.g., a set of image data comprising both input feature vector (e.g., the image data) and an output feature (e.g., a label). Supervised learning may involve processing an input, for example, an image from the digital surgical microscope, and writing out a label in the form of a computer-readable file comprising numeric information. For example, each reference image data may be labeled (e.g., manually) by generating a bounding box around the surgical tools shown in each image frame of the reference surgical video stream. Tools may include, but are not limited to: a scalpel, a knife, forceps (e.g., a tissue forceps, a babcock forceps, a bipolar forceps (Bovie), an Oschner forceps, etc.), a needle, a retractor (e.g., a spinal self-retaining retractor, a handheld retractor, a Senn retractor, a Gelpi retractor, a Weitlaner retractor, etc.), rongeur (e.g., a Kerrison Rongeurs, a Pituitary Rongeur, a Leksel Rongeur, etc.), a hemostats trocar, a Yankauer, a knife handle with or without a blade, a bonnet, a straight and curved hemostats, an iris scissor, a Pennfield freer, a ball tip probe, a nerve hook, a curet, a posterior cobb elevator, an osteotome, etc. The computing device thus receives, for each reference image data, a labeled bounding box around tools (block 303).

At block 304, the computing device may determine, for each labeled reference image data, an output vector based on these labels. For example, the output vector for the bounding box may be represented by values for each of several features. In some embodiments, five numbers that may represent the bounding box may comprise: a class of an object (e.g., the number 0 may be assigned to correspond to "suction cannula"); a location of the center of the box along a Cartesian (e.g., x and y) axis, relative to a pre-established coordinate system of the image (e.g., with the origin at the upper left of the image and the positive x axis proceeding to the right of the image and the positive y axis proceeding toward the bottom of the image); and a width and a height of the bounding box. To make the labeling robust, the location with respect to the x-axis and width numbers may be normalized to the width of the image. Furthermore, the location with respect to the y-axis and the height may be normalized to the height of the image. Thus, an example label might include an array or vector of values such as "0, 0.41, 0.68, 0.85, 0.35". A sixth number may also be used to represent the confidence of the detection as a floating-point number between 0 and 1.

At block 305, the computing device associates the input feature vectors with an input layer of a neural network model and associates the corresponding output vector with the output layer in the neural network model. For example, in the neural network model shown in FIG. 2, the computing device may input values from the reference feature vectors of block 302 into the nodes of input layer 402. The computing device may input values from the output vector thus formed in block 304 on to the output layer 405. The neural network model thus formed, referred to herein as first neural network model, may be distinguishable from a second neural network model formed in method 400 (e.g., shown in FIG. 4), as will be discussed.

At block 306, the computing device may initialize weights in the first neural network model. In some aspects, biases may be initialized and provided for any layer of the first neural network model. The weights and biases may affect an activation function occurring at a node. As will be described, the weights and/or biases may be adjusted based on iterative processes in the training of the first neural network model.

At block 307, the first neural network model may be trained to determine a set of weights corresponding to the relevant features. A first neural network model may be deemed trained, for example, if the model accurately predicts (e.g., to within a threshold level) a location for a bounding box around a tool within image data. A first neural network model may be trained, for example, if it yields an optimized set of weights for use in the application of the trained neural network. The optimized set of weights may be determined through iterative feedforward and backpropagation processes, e.g., as previously described in FIG. 2. As will be described in method 700 (i.e., in FIG. 7), the trained neural network model may be subsequently applied to image data of a live surgical video stream, for the computing device to accurately generate a bounding box around a tool. The trained neural network may then be saved (e.g., to cloud and/or an electronic storage medium) for use in identifying, and/or generating the bounding box around, the tool from the live surgical video stream (block 308).

The bounding box may comprise a rectangle, other quadrilateral, or a circle. Thus, an output vector for the bounding box may include, for example, aspect ratios for the rectangle. Also or alternatively, the output vector for the bounding box may include the length, width, and/or a vertex angle of the quadrilateral, and/or a location of a vertex of the bounding box within the image (e.g., by coordinate). In some embodiments, the bounding box may comprise a square, a circle, or another curved shape. Such embodiments obviate the need to determine aspect ratios (e.g., due to the length and width of a square or a circle being the same) and may thus speed up the training process.

Training Model for the Second Neural Network

FIG. 4 shows a flow diagram of a method of training a deep learning model for detecting a distal end of a tool from image data, according to an example embodiment of the present disclosure. One or more steps of method 400 may be performed by a computing device having a processor. Moreover, the deep learning model trained in method 400 (e.g., referred to herein as a second neural network model or second neural network) may differ from the neural network model trained in method 300, as the second neural network model may be used to detect a distal end of a tool from image data, after the first neural network model has been used to identify the tool (e.g., via a bounding box).

Method 400 may begin with the computing device receiving a plurality of reference image data comprising a bounding box around a tool (block 401). The plurality of reference image data may be obtained from reference surgical videos. In some embodiments, the plurality of reference image data may be those reference image data received in method 300 and already labeled with the bounding box around the tool. For each of the plurality of reference image data, the computing device may generate a reference input feature vector based on relevant features from image data within the bounding box (block 402). Moreover, the image data within the bounding box may correspond to the tool. For example, relevant features may include, but are not limited to, the color of an individual pixel of the image data, a contrast of an individual pixel in relation to neighboring pixels, a brightness of an individual pixel, a degree of similarity with a neighboring pixel, a curvature. In some embodiments, for example, where a convolutional neural network model is to be implemented, the feature vectors may be automatically determined based on the convolved image data. In such embodiments, the relevant features may not necessarily be features that a human could relate to.

In order to train the second neural network model to detect a distal end of a tool (e.g., when image data is fed into the model), each reference image data may be labeled so as to indicate the distal end of the tool. The labeling may be done manually and then stored in the computing device as training data. The computing device may thus receive this labeled reference image data (block 403). In some aspects, the computing device may receive the plurality of reference image data earlier at block 401 as already having the labeled distal end of the tool. The computing device may determine, for each labeled image data, a reference output feature vector based on the distal end of the tool (block 404). In some embodiments, the output feature vector comprises a set of values indicating a location, within the bounding box, of the distal end of the tool. In some aspects, the set of values further includes a direction of (e.g., trajectory) of movement of the distal end of the tool.

At block 405, the computing device associates the input feature vectors with an input layer and associates the corresponding reference output feature vector with the output later in a second neural network. For example, in the neural network model shown in FIG. 1, the computing device inputs values from the reference input feature vectors of block 402 into the nodes of input layer 202. The computing device may input values from the reference output feature vector thus formed in block 405 on to the output later 406. Moreover, the resulting neural network (second neural network) is different from the neural network formed in method 300, as the purpose, and the underlying training data used for that purpose, is different. Whereas the training data in method 300 includes reference input feature vectors associated with relevant features of reference image data mapped to reference output feature vectors associated with the bounding box around a tool, the training data in method 400 includes reference input feature vectors associated with image data within a bounding box around a tool mapped to reference output feature vectors associated with a distal end of the tool.

At block 406, the computing device may initialize weights in the second neural network. In some aspects, biases may be initialized and provided for any layer of the neural network. The weights and biases may affect an activation function occurring at a node. As will be described, the weights and/or biases may be adjusted based on iterative processes in the training of the neural network model.

At block 407, the computing device may train the second neural network model to determine a set of weights corresponding to the relevant features. The second neural network model may be deemed trained, for example, if the model may accurately predict (e.g., to within a threshold level) a location for a distal end of a tool from image data of a bounding box around the tool. Furthermore, the second neural network may be trained, for example, if it yields an optimized set of weights for use in the application of the second trained neural network to determine a distal end point in a tool shown in a live surgical video stream. The optimized set of weights may be determined through iterative feedforward and backpropagation processes, e.g., as previously described in FIG. 4. As will be described in method 500 (e.g., in FIG. 5), the second trained neural network model may be subsequently applied to image data of a live surgical video stream, for the computing device to accurately identify a distal end of a tool to allow the digital surgical camera to track it. The second trained neural network may then be saved (e.g., to cloud and/or an electronic storage medium) for use in identifying, and/or tracking the distal end of the tool from the live surgical video stream (block 408). According to embodiments described herein, finder marks, such as those embodied in a QR code or another fiducial element, are not used to identify and/or label tools.

Operation of the Neural Network Object Detector

FIG. 5 shows a flow diagram of a method of applying deep learning models for detecting and tracking a tool from image data in real-time, according to an example embodiment of the present disclosure. One or more steps of method 500 may be performed by a computing device having a processor. For example, the digital surgical microscope may comprise or may be associated with the computing device. In some embodiments, the computing device performing the training of the neural network models (e.g., training of the first and second neural network models as illustrated in FIGS. 3 and 4, respectively) may also apply the trained neural network models in method 500. Alternatively, the training of one or more of the neural network models may be performed by another computing device or may be performed externally.

Method 500 may begin with the computing device receiving, in real-time, image data of a surgical video stream captured by a digital surgical microscope (block 502). For example, as a surgeon begins a surgical procedure, the digital surgical microscope may begin recording the surgical site. The field of view of the surgical site may include one or more surgical tools. The recording may generate a surgical video stream comprising a plurality of image data (e.g., a plurality of image frames in formats readable by the computing device). Each image data (e.g., image frame) may be presented to the computing device in real-time. The computing device may determine if there is a displacement (e.g., of a tool or other feature in the field of view) based on the received image data (block 504). For example, the computing device may compare a received image data, and a previously received image data, and determine whether the image data fails to satisfy a similarity threshold, such that a failure may indicate a displacement. The computing device may continue to receive image data of the surgical video stream until there is a displacement.

At block 508, the computing device may apply the input feature vector to the first trained neural network to determine an output feature vector. For example, the first trained neural network (e.g., stored at block 308 of method 300) may be retrieved from an electronic storage medium (e.g., of the computing device or an external system that trained the first neural network model). The first trained neural network model may also include a set of weights and/or biases optimized over the training process to be able to allow the neural network model to effectively determine the location of a bounding box around a tool from image data. As previously discussed, a supervised neural network model undergoes training based on training data comprising known reference output vectors for known reference input feature vectors, as was illustrated via methods 300 and 400. After the neural network model is trained, the trained neural network may be used to determine an unknown output feature vector using a known input feature vector. Thus, the input feature vector formed in block 506 may be applied to the first trained neural network model to determine an output feature vector. As the first trained neural network model was trained to identify a bounding box around a tool of from image data, the output feature vector may indicate a location for a bounding box around a tool (e.g., using a set of values formed by the output feature vector).

At block 510, the computing device may generate, based on the output feature vector (e.g., thus generated from the first trained neural network model), an image data having a bounding box around the tool. For example, the location of the bounding box may be determined from a set of values represented by the output feature vector determined in block 508. For example, the set of values may include: a class of an object (e.g. the number 0 may be assigned to correspond to "suction cannula"); a location of the center of the box along a Cartesian (e.g., x and y) axis, relative to a pre-established coordinate system of the image (for example with the origin at the upper left of the image and the positive x axis proceeding to the right of the image and the positive x axis proceeding toward the bottom of the image; and a width and a height of the bounding box. After the bounding box overlaid on the image data around a tool depicted in the image data, the resulting image data formed may comprise the added image data. In some embodiments, a tool may include but is not limited to, for example: a scalpel, a knife, forceps (e.g., a tissue forceps, a babcock forceps, a bipolar forceps (Bovie), an Oschner forceps, etc.), a needle, a retractor (e.g., a spinal self-retaining retractor, a handheld retractor, a Senn retractor, a Gelpi retractor, a Weitlaner retractor, etc.), rongeur (e.g., a Kerrison Rongeurs, a Pituitary Rongeur, a Leksel Rongeur, etc.), a hemostats trocar, a Yankauer, a knife handle with or without a blade, a bonnet, a straight and curved hemostats, an iris scissor, a Pennfield freer, a ball tip probe, a nerve hook, a curet, a posterior cobb elevator, an osteotome, etc., Each bounding box may comprise a label (e.g., a name) indicating the specific tool within the bounding box.

From the image data with added information, the computing device may generate a second input feature vector based on the image data comprising (or comprised within) the bounding box around the tool (block 512). In some aspects, the second input feature vector may be based on relevant features of image data inside the bounding box (e.g., including physical aspects of the tool). The relevant features may include, but are not limited to, the color of an individual pixel of the image data inside the bounding box, a contrast of an individual pixel in relation to neighboring pixels inside the bounding box, a brightness of an individual pixel inside the bounding box, a degree of similarity with a neighboring pixel inside the bounding box, a curvature inside the bounding box, etc. In some embodiments, for example, where the second input feature vector is to be applied to a trained convolutional neural network model (e.g., if the second trained neural network model is a convolutional neural network), the specific feature may be automatically determined based on the convolved image data. In such embodiments, the relevant features may not necessarily be features that a human could relate to.

At block 514, the second input feature vector may be applied to the second trained neural network model to determine the second output feature vector. For example, the second trained neural network (e.g., stored as explained in block 408 of method 400) may be retrieved from an electronic storage medium (e.g., of the computing device or an external system that trained the first neural network model). The second trained neural network model may also include a set of weights and/or biases optimized over the training process to be able to allow the second neural network model to effectively determine a distal end point of a tool from image data. In some aspects, the second output feature vector may comprise a set of values indicating a location (e.g., Cartesian coordinates) of the distal end of the tool in the image data with a bounding box surrounding the distal end of the tool. The outputs from the neural network include a bounding box around the distal end of the tool with the coordinate of the center (x coordinate, y coordinate), width and height of the bounding box, class label (indicating the type of tool), and confidence score of the detection (and/or in the image data received at block 502). The computing device may thus detect the distal end of the tool in the image data (block 516).

At block 518, the computing device may cause the digital surgical microscope to track the distal end of the tool. For example, the digital surgical microscope may be moved so that the detected distal end of the tool is at the center of the field of view of the digital surgical microscope. Also or alternatively, the computing device may cause the digital surgical microscope to track a point that is near to, or speculated to be contacted by, the distal end of the tool. For example, the point may be at a predetermined distance from the detected distal end of the tool in a direction towards a patient anatomy. The predetermined distance may be between 2 pixels and 50 pixels, for example, to the right or upper-right of a detected distal end of the tool. Tracking such a point may allow the digital surgical microscope to predict a surgeon's next area of focus and may cause the digital surgical microscope camera to be directed there. Thereafter, the computing device may continue to receive image data of the surgical video stream (block 502) and may continue to monitor if there are any displacements (block 504), e.g., to cause the digital surgical microscope to redirect its focus, using the methods discussed. This feature is optional, the surgical microscope may remain stationary during the recording period.

In some cases, more than one tool is present in each image. To cause the digital surgical microscope to refocus, one tool may be chosen as the tool to focus on, such that the digital surgical microscope would refocus on that tool. Since moving the digital surgical microscope is optional, the tool to focus on can be set depending on the particular need in the surgery, since each surgery may place an important role in a different tool. The method may provide a user interface such that the user can choose which tool to focus on and to change the tool while the method is in process, such that the focus can be placed on a different tool at a different stage of a surgery.

Artificial Image Update Software

In embodiments described herein, a software to provide artificial update of tool locations in images of a video stream using a Kalman filter for prediction of tool locations is provided, this image prediction software works in parallel with the first and second neural network. Upon receiving an image, the image prediction software calculates Camera Motion Compensation (CMC), which is used to update a trajectory for each tool found in successive frames and uses Kalman filters to predict the location of tools then sends the predicted tool locations to a user interface for display. The image prediction software calculates the CMC matrix needed, using information concerning how features moved in an image frame and a previous frame. CMC is calculated using optical flow or Oriented FAST and Rotated BRIEF (ORB) technique. The trajectories for each tool are updated with the CMC matrix and a Kalman filter is present and associated with each trajectory to predict locations of tools. For images processed by both the image prediction software branch and the neural network object detector, the prediction results from the Kalman filters are compared with detection from the neural network object detector to match the prediction and the detection to create, delete, or update states of the trajectory. Outputs from the image prediction software branch include the bounding box location (coordinate) and size (width and height), and velocity of the bounding box and/or velocity of the bounding box size change.

Camera Motion Compensation (CMC) Calculation

In ORB (Oriented FAST Rotated BRIEF) technique, one implementation of FAST (Features from Accelerated and Segments Test) finds a key point by identifying a pixel p having more than 8 contiguous pixels, among 16 pixels surrounding pixel p, lighter or darker than pixel p. Key points found by FAST are used to determine edges of an image, and the number of contiguous pixels can also be increased to isolate all pixel locations that contain a corner, e.g., 9 contiguous pixels among 16 pixels. FAST uses a multiscale image pyramid and detects key points at each level of the pyramid, thereby locating key points at different scales.

After locating key points, ORB assigns an orientation to each key point, depending on the levels of intensity change around that key point. To detect intensity change, ORB uses intensity centroid, which assumes that a corner's intensity is offset from its center, and this vector is used to impute an orientation. From this, the centroid can be found, and a vector from the corner's center to the centroid can be constructed. The orientation of the patch is calculated therefrom.

BRIEF (Binary robust independent elementary feature) takes all key points found by FAST and converts them into binary feature vectors, also known as binary feature descriptors, which represent an object. BRIEF starts by smoothing the image using a Gaussian kernel in order to prevent the descriptors from being sensitive to high-frequency noise, then selects a random pair of pixels in a defined neighborhood around that key point, the defined neighborhood around that pixel is called a patch. The first pixel in the random pair is drawn from a Gaussian distribution centered around the key point with a stranded deviation or spread of sigma. The second pixel in the random pair is drawn from a Gaussian distribution centered around the first pixel with a standard deviation or spread of sigma by two. If the first pixel is brighter than the second, it is assigned the value of 1, if not, it is assigned the value of 0. This process of selecting a random pair is repeated 128 times for each key point in a 128-bit vector. BRIEF creates a vector for each key point in an image. The longer the vector, the more that pixel will move. CMC studies how key points have moved between two images by first matching them and then determining their rotation and translation between images. By iteratively determining this transformation, CMC is calculated as the transformation of the image that occurred between consecutive frames.

Optical flow computes a vector that describes the movement of a pixel or feature in an image. There are two types of optical flow, dense and sparse. Dense optical flow calculates a vector that describes how a pixel moves. Dense optical flow can be performed for up to "N" pixels, with N being the total number of pixels in the image. This method is computationally expensive. Sparse optical flow calculates vectors for some features in an image. Sparse optical flow requires less computational power and is used herein, such that the optical flow calculation can be performed at higher frequencies.

In the image prediction software, to calculate optical flow, the process starts with finding feature points in a previous frame. Feature points are points of interest which have a high level of image content information, such as corner, edge, indentation, etc. For each feature point, the method calculates image gradient locally around the feature point. Then spatial gradient is calculated using the X and Y image gradients from the previous frame. Spatial gradient is a gradient with components being the rate of change of a quantity in space. In the method herein, spatial gradient is a gradient with components being the rate of change of pixels in space. For each feature point, temporal gradient is calculated with both frames. The optical flow vector for each feature point is calculated with the image gradient, the spatial gradient, and the temporal gradient of each feature point. The optical flow vector gives an estimate of the new position of the feature point in the current frame. This new position is checked for validity. For example, a validity check could be a motion constraint that enforces a maximum possible magnitude for the optical flow vector. If the calculated vector is too large and exceeds the maximum, the magnitude of the vector is set to 0 or a predefined limit. If the new position is valid, the new position becomes the position of the feature point in the next frame.

Optical flow vector calculation is performed for each feature point. Once all feature points are matched between the previous frame and the current frame, the transformation from the previous frame to the current frame is calculated. The calculated transformation is the CMC.

CMC calculation produces a CMC matrix, which describes translation and rotation of image key points between frames. Each of the tools within the images has a trajectory, and information extracted from the images is used to help initialize and update trajectories. Within each trajectory, a Kalman filter is present to predict the next location of each tool tip.

Tool Trajectory Component

In embodiments, within the image prediction software, a tool trajectory component is provided to track information concerning each tool present in the surgical scene. When the computer programming product according to embodiments herein initializes, for each tool prediction, the matching algorithm component initializes a tool trajectory. Each tool trajectory has an associated Kalman filter. Each tool trajectory component uses the associated Kalman filter for prediction of the locations and sizes of the bounding box associated with the tool tip. The matching algorithm updates the state of the tool trajectory.

The matching algorithm, after performing its matching step, sends information concerning the match results to the tool trajectory component. In a particular image with tools processed and sent by the Kalman filter to the matching algorithm, each tool has a trajectory. If a tool is matched by the matching algorithm, the information is sent back to the tool trajectory component, and its trajectory is updated, if there is an update. The matched tool is assigned a state of "present" by the tool trajectory component. If a tool is not detected by the neural network, after a few frames of continuous non-detection, the tool is assigned a state of "missing" by the tool trajectory component. If a tool is not detected by the neural network, after a significant number of frames of continuous non-detection, the tool is assigned a state of "lost" by the tool trajectory component. If a tool is not detected by the neural network, after an extended period of frames of continuous non-detection, the tool is assigned a state of "gone forever" by the tool trajectory component. The number of frames and the time length for each detection state may be set within the image prediction software but shall reflect the reality of a surgical scene.

Operation of Kalman Filter

The Kalman filter uses a system's dynamic model, or physical laws of motion, known control inputs to the system, (e.g., adjustment in camera motion speed), changes in lighting conditions, and multiple sequential measurements (e.g., detection of tool tip from the neural network) to form an estimate of the system's current state (e.g., the current center coordinate, width, and height of the bounding box, the velocity of the bounding box, and the velocity of the bounding box size change). The Kalman filter also calculates weighted averages from covariance, a measure of the estimated uncertainty of the prediction of the system's state.

In embodiments described herein, the image prediction software branch uses an internal Kalman filter associated to each trajectory to predict the next location of the surgical tool tip. The Kalman filter works by a two-phase process, which is the prediction phase and an update phase. In the prediction phase, the Kalman filter produces estimates of the current state variables and the uncertainties (covariances) with the state. The current state variables describe the coordinate of the bounding box, the width and height of the bounding box, the velocity of the bounding box, and/or the velocity of the bounding box size changes (how fast the bounding box changes in size). The bounding box size may be set to be unchanged, therefore the velocity of the bounding box size changes is always the same. The velocity of the bounding box may also be set to a constant. The uncertainties describe how confident the Kalman filter is that the current prediction is accurate. This prediction is based on the detections from the immediate previous frame by the neural network and information extracted from the current image. The prediction can be output to a user interface for viewing.

After the prediction step, if a detection is available, the update step occurs. During the update step, the Kalman filter receives the location (coordinate), dimensions (width and height), class label, and confidence of the bounding box from the neural network detection. Based on this information and the previous state (i.e., the previous detection from the immediate previous frame), the current state (location, label, size of the bounding box) and covariance (uncertainties) are updated.

As the neural network object detector detects tool tips and places a bounding box around the detected tool tips in an image it processes, the neural network's detection is used as a new measurement in an update step in the Kalman filter. The new measurements (e.g., the bounding box location (coordinate and center), the bounding box size (width and height), confidence, and class label) are incorporated to refine the predicted state. In particular, the predicted state and the new measurement are combined using a weighted average, with weights indicating estimated uncertainty.

Operation of Matching Algorithm

In certain embodiments, a matching algorithm is provided to match the tool tip detected from the neural network with the tool tip prediction from the Kalman filter. For each frame processed by both the neural network and the image prediction software, a matching algorithm matches detected tool tips from the neural network object detector with predicted tool tips from the Kalman filter. Depending on the result of matching, the matching algorithm creates new trajectories, deletes trajectories, or update states of trajectories.

After the neural network object detector has processed an image frame and detected tool tips within that image frame, a bounding box is placed on each tool tip with a label for each tool tip. The data concerning the tool tip as detected, namely, the bounding box, is sent to the matching algorithm. At the same time, the prediction of the bounding box as outputted by the Kalman filter within the image prediction software is also sent to the matching algorithm. The matching algorithm receives the information concerning the bounding box as processed by two different methods and performs matching.

In particular, the matching algorithm receives data concerning the actual tool detection from the neural network object detector, namely, a bounding box on each tool tip, and the bounding box is characterized by coordinate, center, width, and height. The matching algorithm also receives the same data concerning the bounding box, but this data is the result of prediction by the image prediction software branch. The matching algorithm matches the two datasets by comparing, for each bounding box on each tool tip, the coordinate, center, width, and height of the bounding box.

The matching algorithm uses a plurality of parameters to compare the detection from the neural network object detector and the prediction from Kalman filter. The dimensions of tool tips, distance between specific points, weights for different heuristics are examples of parameters used by the matching algorithm to compare the data as detected by the neural network and the data as predicted by the Kalman filter. At the beginning of the matching process, parameters are set up, optionally with defined values such as maximum distance tolerable between specific points.

For each tool tip detected in the image processed by the neural network, the matching algorithm calculates a score based on Euclidean pixel distances between each detected tool and all existing trajectories, bounding box size difference, and confidence difference from existing trajectories. Bounding box size difference and confidence difference are given less weight than Euclidean pixel distances. The bounding box size difference, confident difference, and Euclidean distance are combined to form a heuristic distance. The heuristic distance is used as a key in a key value pair with the detection and existing trajectory. Each detection and existing trajectory pair are stored. The matching algorithm sorts these pairs by heuristic and iterates through the pairs, matching each detection to the closest available trajectory. Trajectories with the best matches are updated, which is, the Kalman filter performs the update step with the information from the neural network object detector, namely, the coordinate, center, width, and height of the bounding box, class label, and confidence, as received from the neural network object detector by the Kalman filter. If a new tool tip is detected by the neural network object detector but not predicted by the Kalman filter, i.e., a detection exists but is not matched with a trajectory, a new trajectory is created for the newly detected tool tip. If a tool tip is no longer detected by the neural network but predicted by the Kalman filter, i.e., a trajectory exists but is not matched with a detection, the tool is no longer present on the surgical scene, and after a predetermined number of frames, the trajectory associated with it is removed. If a trajectory is matched with a detection, the trajectory is updated with information from the detection by the neural network object detector and the information is given to the Kalman filter to update the Kalman filter. This approach allows for tracking multiple objects over time, handling new objects entering the scene and removing objects disappearing from the scene.

Operation of the Neural Network and the Artificial Image Update Software

In embodiments, images are sent to the software described herein at X frequency to the neural network and at Y frequency to the image prediction software, and $X \leq Y$. Thus, when an image is received at the image prediction software, it may not be received at the neural network, depending on the frequency that the system is set at.

In various embodiments, an image prediction software for image processing processes images from a video feed having a neural network object detector branch and an image prediction software branch is provided as described herein. A neural network object detector processes images at a certain frequency calculated at frames per second. The image prediction software for image processing can process images at a different and faster rate. For a feed of images at a certain frequency, both the neural network object detector and the image prediction software can process a first image, then only the image prediction software processes a second image, and optionally a third, fourth, or more images, until the nth image, then at the $(n+1)^{th}$ image, both the neural network object detector and the image prediction software can process the $(n+1)^{th}$ image. The output track will consist of the first processed image, the second processed image until the nth processed image, then the $(n+1)^{th}$ processed image. The value of n is determinative of the order of frequency difference between the neural network object detector and the image prediction software. For example, if n=4 then the processing frequency of the image prediction software is four times the processing frequency of the neural network object detector, if n=5 then the processing frequency of the image prediction software is five times the processing frequency of the neural network object detector.

In an embodiment described herein, the neural network object detector is set at 15 FPS, such that it processes 15 images per second. The image prediction software is set at 60 FPS, such that it processes 60 images per second. The frequency chosen for the neural network object detector takes into account the computing power of the computing article on which the software runs and the processing speed of the software. Ideally, the image prediction software processes more images than or equal to the neural network object detector.

In an embodiment, a camera records a video at the frequency of 60 FPS, the camera captures an image and transmits it to the CPU, the image labeled as image frame #1, which is an image of a surgical site and contains at least one surgical tool. Image frame #1 is passed as input into a neural network object detector set at 15 FPS. The same image frame #1 is passed as input into the image prediction software, which is set at 60 FPS.

In an embodiment described herein, the neural network object detector operates at a lower frequency than the image prediction software. For every image that the neural network object detector processes, the image prediction software processes at least one additional image. In one such embodiment, the neural network object detector is set at 15 FPS and the image prediction software is set at 30 FPS, the image prediction software operates at a frequency that is 2 times higher than the frequency of the neural network object detector. Thus, the next images (image #2) are sent to the image prediction software and not the neural network object detector. Upon receipt of image #2, the image prediction software calculates the CMC needed based on how features in image #2 are moved as compared to image #1. CMC is calculated using optical flow or ORB. The image prediction software then uses its internal Kalman filter to predict the next location of the tools in image #2 and produces a bounding box around each tool. Image #2 with prediction produced by the Kalman filter is then shown to the user at the user interface. For image #2, the neural network object detector does not process these images, and thus the output image #2 shown to the user is an image processed by the image prediction software only.

When image #3 is received, both the neural network object detector and the image prediction software process image #3. The image prediction software calculates camera motion compensation using the CMC algorithm then predicts the next location of the tool tips using the Kalman filter within each tool trajectory algorithm. The image with Kalman filter prediction is sent to the matching algorithm. Meanwhile, the neural network object detector also processes image #3 and places a bounding box around the tool tips detected in image #3. The data of image #3 as processed by the neural network object detector is sent to the matching algorithm. The matching algorithm compares trajectories predicted by the Kalman filter with detected tools by the neural network and matches them together. Matched trajectories are updated with new parameters from the detection. Unmatched trajectories are marked as missing, which will be deleted after a period of time of continuous missing. New trajectories are created for unmatched detected tools.

Figure 6:
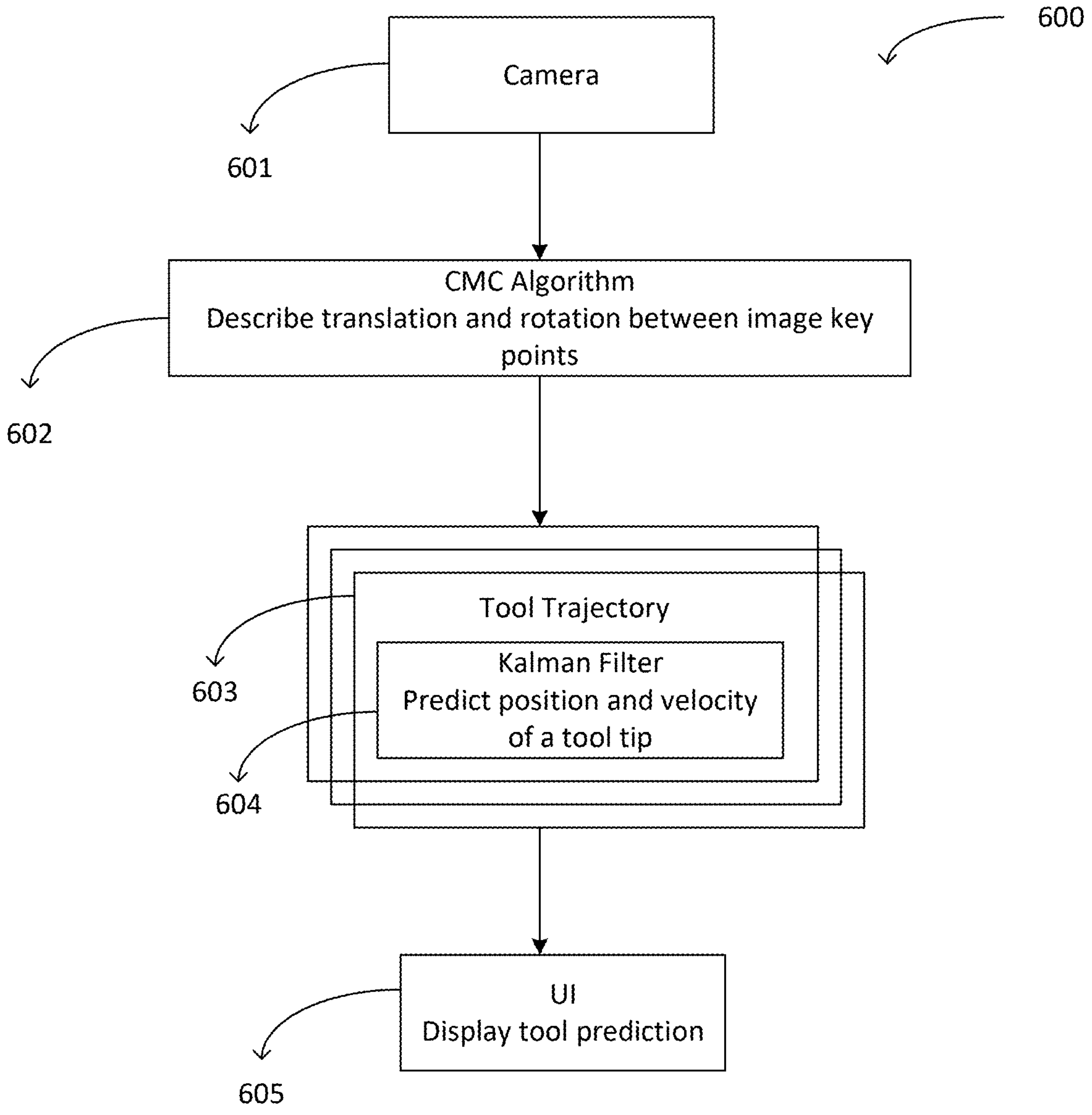
FIG. 6 depicts a flow diagram of a method to process an image and artificially update tool location in that image using camera compensation motion and Kalman filter.

FIG. 6 illustrates method 600 wherein the image prediction software branch processes an image received when the neural network object detector does not receive the same image. One or more steps of method 600 may be performed by a computing device having a processor. For example, the digital surgical microscope may comprise or may be associated with the computing device. In some embodiments, the computing device that performs the training of the neural network models (e.g., training of the first and second neural network models as illustrated in FIGS. 3 and 4, respectively) may also apply this method 600. Alternatively, the training of one or more of the neural network models may be performed by another computing device or may be performed externally.

Method 600 begins with the computing device receiving, in real-time, image data of a surgical video stream captured by a digital surgical microscope (block 601). For example, as a surgeon begins a surgical procedure, the digital surgical microscope may begin recording the surgical site and send images captured in real time to a computing article configured to execute the method described herein. The field of view of the surgical site may include one or more surgical tools. The recording generates a surgical video stream comprising a plurality of image data (e.g., a plurality of image frames in formats readable by the computing device). Each image frame is presented to the computing device in real-time.

In method 600, the image is received in the CMC algorithm and processed to generate a CMC matrix. The CMC matrix describes translation and rotation between key points within the image. Method 600 uses either ORB technique or optical flow to generate CMC matrix at step 602. When ORB (Oriented FAST Rotated BRIEF) technique is applied, FAST determines key points by identifying a pixel p having more than 8 among 16 surrounding pixels lighter or darker than pixel p. After locating key points, ORB assigns an orientation to each key point, depending on the levels of intensity change around that key point. To detect intensity, ORB uses intensity centroid to determine a vector from the corner's center to the centroid. With this vector for each key point, the orientation of a patch is calculated.

After FAST has determined the key points, BRIEF is used to generate a CMC matrix. After locating key points, BRIEF converts the key points into binary feature vectors or binary feature descriptors. BRIEF smooths the image using a Gaussian kernel and creates a vector for each key point in the image. The longer the vector, the more that pixel will move. CMC matrix is generated by first matching key points between two images and then determining their rotation and translation between images. By iteratively determining this transformation, CMC is calculated as the transformation of the image that occurred between consecutive frames.

When optical flow method is used in step 602, optical flow method calculates optic flow vector for a point, which is a vector describing movement of a point. Feature points are identified and image gradient around each feature point is calculated. Then, spatial gradient is calculated on the previous frame and temporal gradient is calculated with both the previous frame and the current frame. The optical flow vector is calculated for each feature point, using the image gradient, the spatial gradient and the temporal gradient. Once all feature points are matched between the previous frame and the current frame, the transformation from the previous frame to the current frame is calculated. The calculated transformation is the CMC.

For each tool in the surgical site captured by the camera, the image prediction software creates a trajectory, which represents data tracking the movement of each tool. Step 603 is shown as multiple components, which represents multiple trajectories for multiple tools. Each trajectory is specific to each tool and has a Kalman filter 604 calculation step embedded in it. The Kalman filter 604 conducts steps to predict the location of the bounding box surrounding the tool tip belonging to that particular trajectory at present time.

In FIG. 6, the image prediction software branch processes the image received by itself, since this is an image received in the image prediction software only and not the neural network. While a Kalman filter operates in two steps, prediction and update, in method 600, the Kalman filter 604 only conducts the prediction step. The Kalman filter 604 receives the class label, the bounding box location (coordinate and center), the bounding box size (width and height). The bounding box may also have a set of values represented by the output feature vector in step 516 of FIG. 5. For example, the set of values may include: a class of an object (e.g. the number 0 may be assigned to correspond to "suction cannula"); a location of the center of the box along a Cartesian (e.g., x and y) axis, relative to a pre-established coordinate system of the image (for example with the origin at the upper left of the image and the positive x axis proceeding to the right of the image and the positive y axis proceeding toward the bottom of the image); a width and a height of the bounding box, and a confidence value. Using the system model (e.g., motion model based on physical laws, adjustment in camera motion speed, changes in lighting conditions, multiple sequential measurements (e.g., detection of tool tip from the neural network, previous data on movement of similar tools in similar surgeries, other data concerning surgical tools, etc.), the Kalman filter 604 estimates the current state based on the previous state and the CMC, which is, to estimate the current coordinate, center, width, and height of the bounding box, together with the velocity of the bounding box from the previous coordinate, center, width, and height of the bounding box, and the previous velocity of the bounding box. In some embodiments, the tool(s) may include but is not limited to, for example: a scalpel, a knife, forceps (e.g., a tissue forceps, a babcock forceps, a bipolar forceps (Bovie), an Oschner forceps, etc.), a needle, a retractor (e.g., a spinal self-retaining retractor, a handheld retractor, a Senn retractor, a Gelpi retractor, a Weitlaner retractor, etc.), rongeur (e.g., a Kerrison Rongeurs, a Pituitary Rongeur, a Leksel Rongeur, etc.), a hemostats trocar, a Yankauer, a knife handle with or without a blade, a bonnet, a straight and curved pair of hemostats, an iris scissor, a Pennfield freer, a ball tip probe, a nerve hook, a curet, a posterior cobb elevator, an osteotome, etc. Each bounding box may comprise a label indicating the specific tool within the bounding box. The presently described embodiments permit labeling multiple tools within the same class (e.g., scalpels) and/or multiple tools within different classes (e.g., scalpels, needles, retractors, etc.). The system model includes dynamic model (physical laws of motion), known control inputs to the system, (e.g., adjustment in camera motion speed), changes in lighting conditions, and multiple sequential measurements (e.g., detection of tool tip from the neural network) to form an estimate of the system's current state (e.g., the current coordinate, center, width, and height of the bounding box, the velocity of the bounding box, the velocity of the bounding box size change). The Kalman filter 604 also calculates weighted averages from covariance, a measure of the estimated uncertainty of the prediction of the system's state and stores the covariances for future use. The prediction from the Kalman filter 604 is sent to a user interface and output on an image for viewing by a user.

The user interface 605 displays the bounding box on the image as predicted by the Kalman filter 604. The user interface 605 may be displayed on a physical display, which may be a component of a computing device which conducts the method of FIG. 6. The display may also be a separate component from the computing device which conducts the method of FIG. 6. Conveyance of information from the user interface 605 to the display may be by wire or wireless connection.)

Figure 7:
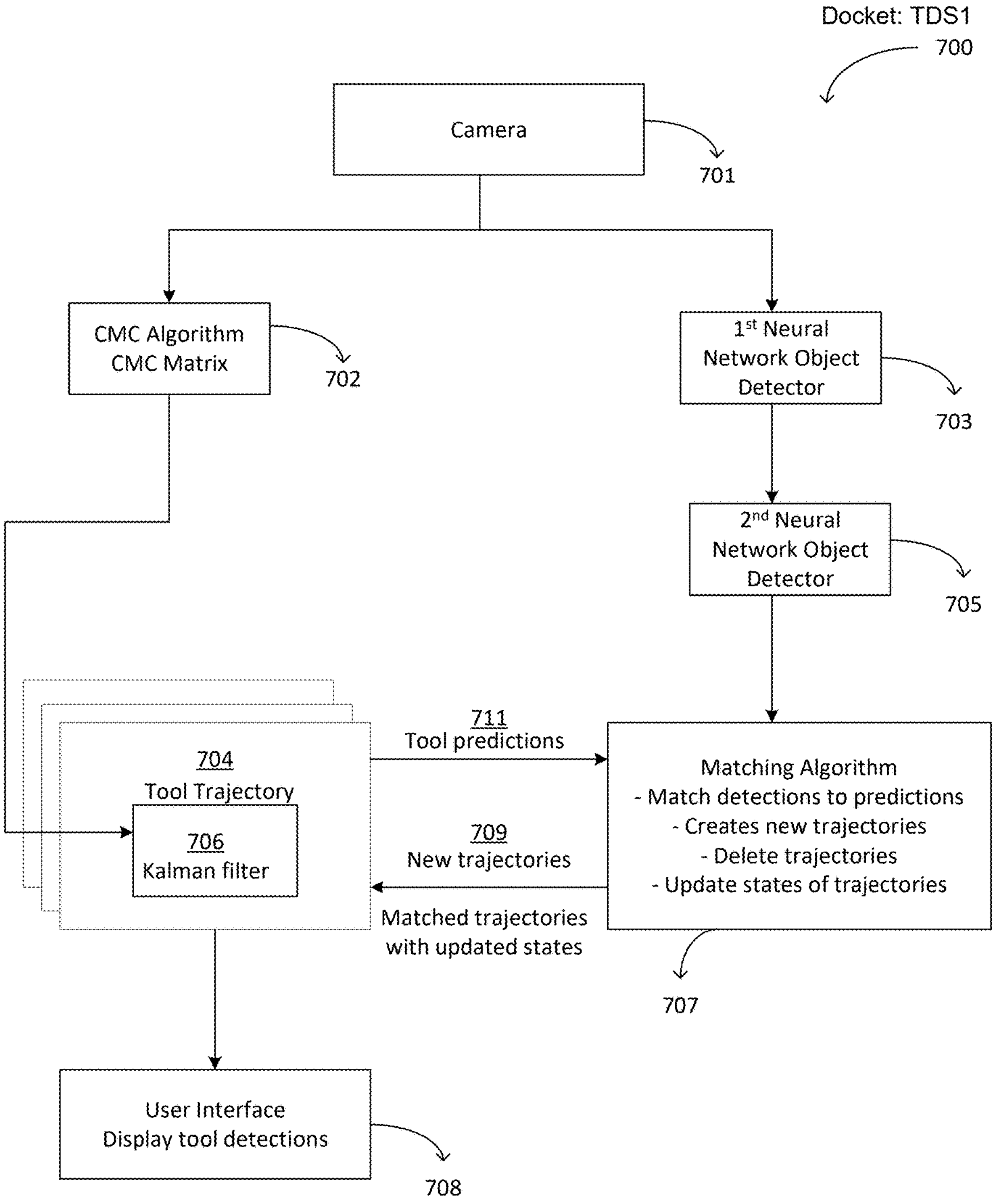
FIG. 7 depicts a flow diagram of applying deep learning models for detecting tool tips and of using camera motion compensation calculation and Kalman filter to predict the next location of tool tips in video display of a surgical site.
Figure 8:
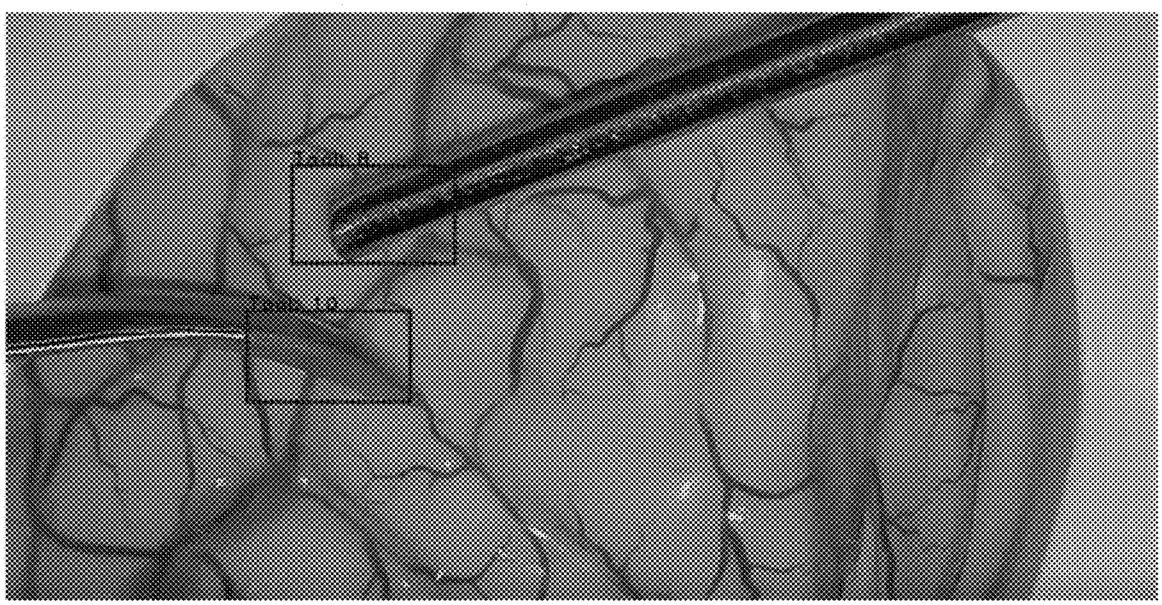
FIG. 8 depicts an output frame from a method according to embodiment herein. This image is frame 4202 from a video feed processed at a frequency of 45 frames per second.
Figure 9:
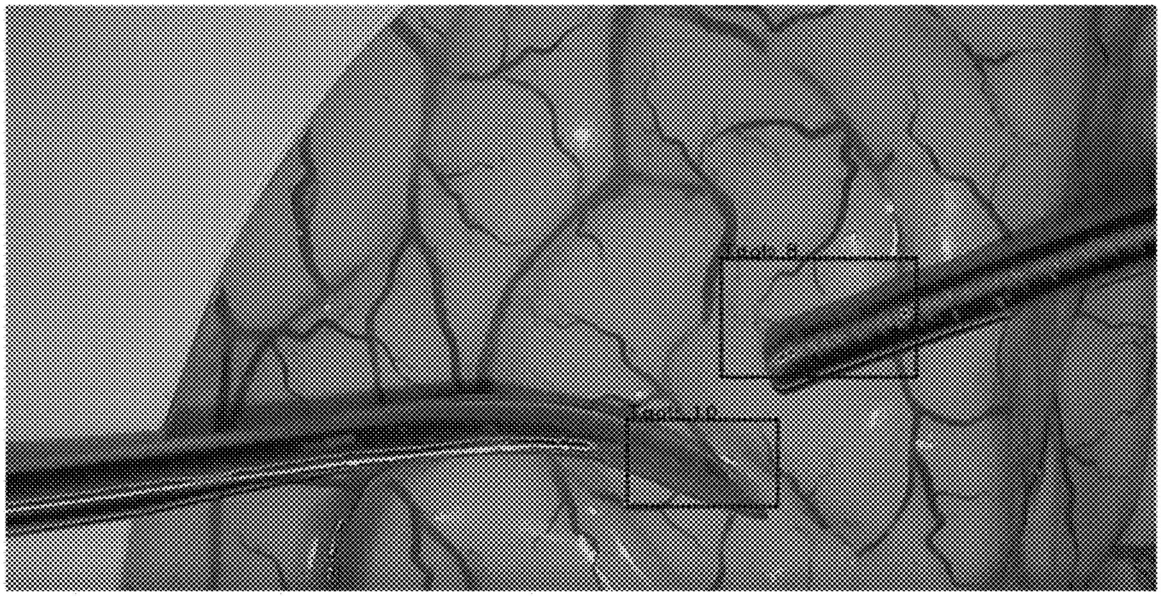
FIG. 9 depicts output frame 4247 from the same video feed as in FIG. 8 as processed according to embodiment herein.
Figure 10:
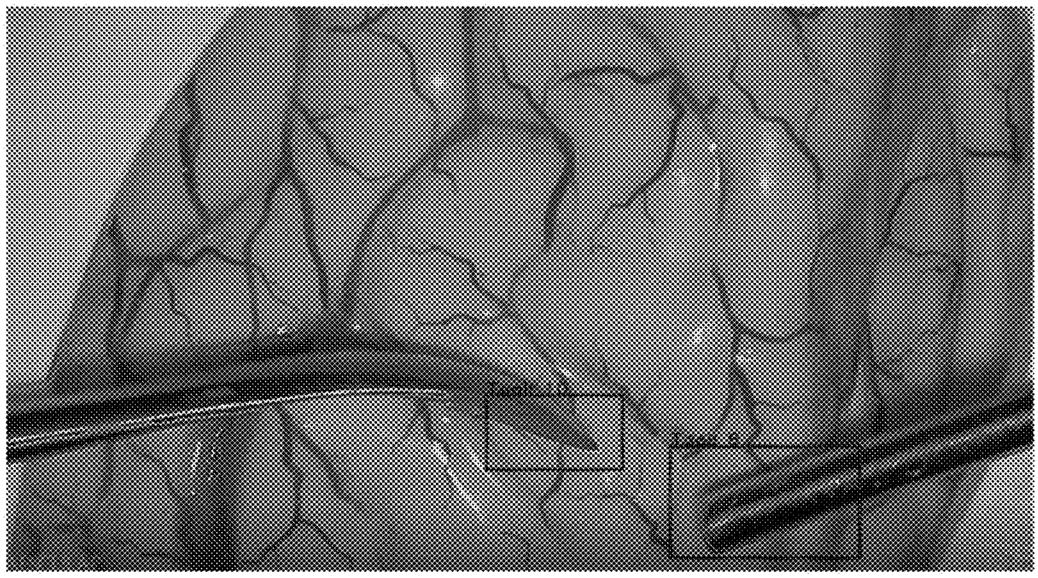
FIG. 10 depicts output frame 4261 from the same video feed as in FIG. 8 as processed according to embodiment herein.

FIG. 7 illustrates the operation of the neural network object detector branch and the image prediction software branch when their image receipt from the camera coincides. The same image is received by both the neural network object detector branch and the image prediction software branch. Both the neural network object detector branch and the image prediction software branch process the same image in parallel before exchanging the results of their respective processing at the matching algorithm 705.

The neural network object detector branch comprises a neural network object detector having the first neural network object detector 703 (e.g., as saved in step 308 of FIG. 3) and the second neural network object detector 705 (e.g., as saved in step 408 of FIG. 4). Alternatively, one neural network trained with functionality of both the first and second neural network object detector as in FIG. 3 and FIG. 4, respectively, may be used. Upon receiving the image in the first neural network object detector, at block 703, the computing device applies the input feature vector to the first trained neural network to determine an output feature vector. As the first trained neural network model was trained to identify a bounding box around a tool from the image data, the output feature vector may indicate a location for a bounding box around a tool (e.g., using a set of values formed by the output feature vector). Then, the computing device generates, based on the output feature vector (e.g., generated from the first trained neural network model), a bounding box around each tool tip with detailed information about the tool tip. The location of the bounding box may be determined from a set of values represented by the output feature vector determined in the previous step. For example, the set of values may include: a class of an object (e.g., the number 0 may be assigned to correspond to "suction cannula"); a location of the center of the box along a Cartesian (e.g., x and y) axis, relative to a pre-established coordinate system of the image (for example with the origin at the upper left of the image and the positive x axis proceeding to the right of the image and the positive y axis proceeding toward the bottom of the image); and a width and a height of the bounding box. In some embodiments, a tool includes but is not limited to, for example: a scalpel, a knife, forceps (e.g., a tissue forceps, a babcock forceps, a bipolar forceps (Bovie), an Oschner forceps, etc.), a needle, a retractor (e.g., a spinal self-retaining retractor, a handheld retractor, a Senn retractor, a Gelpi retractor, a Weitlaner retractor, etc.), rongeur (e.g., a Kerrison Rongeurs, a Pituitary Rongeur, a Leksel Rongeur, etc.), a hemostats trocar, a Yankauer, a knife handle with or without a blade, a bonnet, a straight and curved hemostats, an iris scissor, a Pennfield freer, a ball tip probe, a nerve hook, a curet, a posterior cobb elevator, an osteotome, etc., Each bounding box may comprise a label (e.g., a name) indicating the specific tool within the bounding box.

From the image data, the computing device, at block 705, generates a second input feature vector based on the image data comprising (or comprised within) the bounding box around the tool. Then, the second input feature vector is applied to the second trained neural network model to determine the second output feature vector. In some aspects, the second output feature vector comprises a set of values indicating a location (e.g., Cartesian coordinates) and dimension (width and height) of the bounding box surrounding the distal end of the tool in the image data. In other aspects, the second output feature vector also comprises a set of values indicating a class label of the tool tip and confidence. The computing device thus detects the distal end of the tool in the image data and outputs.

Meanwhile, the image prediction software branch processes the same received image in the same manner as in FIG. 6 but without directly displaying the predicted image to the user interface. Instead, at step 711, the computing device sends the prediction from the Kalman filter 706 to the matching algorithm 707.

In the matching algorithm 707, the computing device compares the prediction from the Kalman filter 706 and the detection from the second neural network object detector 705 for bounding boxes. Bounding boxes in the prediction are compared with bounding boxes in the detection, matched bounding boxes are marked as present. States of the trajectory for each matched bounding boxes as detected by the neural network object detector are updated and data is sent from the matching algorithm to the Kalman filter for use in an update phase. For bounding boxes that are present in the prediction but not in the detection, the matching algorithm marks as missing. This will continue for a few frames, then the unmatched trajectories that are still missing are marked as lost. After an extended time period, or a large number of frames as determined by engineering design, the unmatched trajectories that are lost are marked as gone forever. The computing device deletes the trajectories that are marked as gone forever. For bounding boxes found in detection but not in prediction, the matching algorithm initiates new trajectories to account for the newly detected tool. Trajectories that are output by the matching algorithm are shown by the user interface 708.

In an exemplary embodiment, the image prediction software branch processes images at a frequency of 60 FPS, while the neural network object detector processes only 15 of those images, at a frequency of 15 FPS. The image output to the user would be in a sequence of $1^{st}$ image processed by the neural network object detector and matched with the artificial update branch, $2^{nd}$ image processed by the image prediction software branch only, $3^{rd}$ image processed by the image prediction software branch only, $4^{th}$ image processed by the neural network object detector and matched with the artificial update branch, and repeat. The user thus perceives the track at a rate of 60 FPS, giving a smoother viewing experience.

CMC and Kalman filter calculations can be performed on a CPU at a high speed, for example, at less than 40 milliseconds on an i7-10700 CPU. On a graphic processing unit (GPU), the speed of CMC and Kalman filter calculations can be higher, up to 2-3 order of magnitude higher than on a CPU. Neural networks, on the other hand, are commonly known to be a GPU intensive task. By using the software according to embodiments herein to provide artificial updates of images while waiting for the next image processed by the neural network object detector, the actual output rate of image by the method described herein is higher than the processing rate of the neural network object detector. In an example as described herein, the update rate is 60 FPS while the neural network update rate is 15 FPS, with the image prediction software providing 45 of the 60 frames output per second. The 45 frames output by the image prediction software branch only takes. This increases the update rate while not significantly increasing workload for the processor.

Trajectories outputted by the matching algorithm are displayed at a physical display using a user interface software. Optionally, the user interface software provides an option for the user to hide labels, or change labels, such as the name of the tool, associated numbers, or other identification information can be changed to fit the user's choice.

In certain embodiments, instances of a tool's presence are recorded in images over time and data associated with various characteristics of a tool's movement, e.g., the position, size, trajectory, and popularity of the tool over time, can be tracked and stored. This data can be of great importance in recording treatment processes, retaining medical records for future use, or for use in education and training.

Other features and advantages of the invention will be apparent from the following detailed description, and from the claims.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

We claim:

1. A method of processing video images of a surgical site, the method comprises:

receiving, in real-time, by a computing device having a processor, image data of an image in a surgical video stream comprising a plurality of images captured by a camera of a digital surgical microscope, wherein the surgical video stream shows at least one tool;

determining the order of receipt of the image;

for the first and every $[(n+1)\times i]^{th}$ image:

applying the image data from an image in the surgical video stream to a first trained neural network model to determine a location for a bounding box around a distal end point of each of the at least one tool;

generating processed image data comprising a bounding box around the distal end point of the at least one tool;

applying the processed image data to a second trained neural network model to track the distal end point of each of the at least one tool;

initializing a trajectory for each bounding box and setting up a Kalman filter for each trajectory;

calculating camera motion compensation for the image data received as compared to the image data of an immediate previous image in the surgical video stream;

predicting parameters of the bounding box of each of the at least one tool using the Kalman filter associated with the trajectory;

correcting the prediction of the Kalman filter using the calculated camera motion compensation;

matching the bounding box as generated in the processed image data and the bounding box as predicted by the Kalman filter;

marking a trajectory as present if a bounding box as predicted by the Kalman filter is matched with a bounding box in the processed image data and updating the Kalman filter with the processed image data concerning the matched bounding box;

marking a trajectory as lost if a bounding box as predicted by the Kalman filter is not matched with a bounding box in the processed image data;

sending the present trajectories and the initialized trajectories to a user interface module; and displaying the trajectories at a display using the user interface module;

for every image not the first or $[(n+1)\times i]^{th}$ image:

calculating camera motion compensation for the image data received as compared to the image data of the immediate previous image;

predicting the next parameters of the bounding box of each of the at least one tool using the Kalman filter and the calculated camera motion compensation; and displaying an image using image data from the prediction at a display using the user interface module, wherein n is a predetermined integer and i starts at 1 and increases by 1 each time, wherein the processed image data comprises a location and a size of the bounding box, a label, and the bounding box confidence, wherein the parameters of the bounding box comprise a location, a size, a velocity, and a velocity of size change of the bounding box, and wherein the trajectory is a collection of digital image data concerning a bounding box collected over time.

2. The method of claim 1, wherein the at least one tool is a scalpel, a knife, a pair of forceps, a needle, a retractor, a rongeur, a hemostats trocar, a Yankauer, a knife handle with a blade, a knife handle without a blade, a bonnet, a pair of straight hemostats, a pair of curved hemostats, an iris scissor, a Pennfield freer, a ball tip probe, a nerve hook, a curet, a posterior cobb elevator, or an osteotome.

3. The method of claim 1, wherein applying the image data to the first trained neural network model comprises:

generating a first input feature vector based on the image data; and applying the first input feature vector to the first trained neural network model to generate a first output feature vector, wherein the first output feature vector indicates the location, the size, the label, the velocity, and the velocity of the bounding box size change of the bounding box of each of the at least one tool.

4. The method of claim 1, wherein applying the processed image data to the second trained neural network model comprises:

generating a second input feature vector based on the processed image data; and applying the second input feature vector to the second trained neural network model to generate a second output feature vector, wherein the second output feature vector indicates the location for the distal end of each of the at least one tool.

5. The method of claim 1, wherein calculating camera motion compensation comprises using Oriented FAST Rotated BRIEF technique or sparse optical flow technique.

6. The method of claim 1, wherein updating the Kalman filter comprises updating the location, label, and size of the matched bounding box and updating estimated current state variables using weighted averages.

7. The method of claim 1, wherein the value of n is chosen by a user.

8. The method of claim 1, wherein n is 0.

9. The method of claim 1, further comprising, prior to applying the image data to the first trained neural network model:

receiving a plurality of reference image data of a reference surgical video, wherein each reference image data represents a respective image frame showing a plurality of tools;

generating, for each of the plurality of reference image data, a reference input feature vector indicating relevant features of the reference image data, and a reference output feature vector indicating a label, a location, a size, a velocity, of a velocity of size change of a bounding box around each of the plurality of tools; and training, by associating each reference input feature vector with its respective reference output feature vector, a neural network to form the first trained neural network model.

10. The method of claim 1, further comprising:

identifying, by the computing device, based on a previously received image data of the surgical video stream, a displacement of a feature in the surgical video stream beyond a threshold distance; and choosing one tool among the at least one tool and causing the digital microscope to track the distal end of the chosen one tool, wherein the steps of claim 1 are conducted responsive to the identified displacement.

11. The method of claim 1, further comprising:

setting a value reflecting how many times a trajectory is marked as lost before removing a trajectory;

counting the times a trajectory is marked as lost; and removing the trajectory when the times have reached the value, wherein the value is an integer.

12. A system for processing video images of a surgical site in real-time, the system comprises a digital surgical microscope (DSM) comprising a DSM camera; a processor; and a memory device storing computer-executable instructions that, when executed by the processor, causes the processor to:

receive, in real-time, by a computing device having a processor, image data of an image in a surgical video stream captured by a camera of the digital surgical microscope, wherein the surgical video stream shows at least one tool;

determine the order of receipt of the image;

for the first and every $[(n+1)\times i]^{th}$ image:

apply the image data to a first trained neural network model to determine a location for a bounding box around a distal end point of each of the at least one tool;

generate processed image data comprising a bounding box around the distal end of the at least one tool;

apply the processed image data to a second trained neural network model to track the distal end point of each of the at least one tool;

initialize a trajectory for each bounding box and setting up a Kalman filter for each trajectory;

calculate camera motion compensation for the image data received as compared to the image data of an immediate previous image;

predict parameters of the bounding box of each of the at least one tool using the Kalman filter associated with the trajectory;

correct the prediction of the Kalman filter using the calculated camera motion compensation;

match the bounding box as generated in the processed image data and the bounding box as predicted by the Kalman filter;

mark a trajectory as present if a bounding box as predicted by the Kalman filter is matched with a bounding box in the processed image data and updating the Kalman filter with the processed image data concerning the matched bounding box;

mark a trajectory as lost if a bounding box as predicted by the Kalman filter is not matched with a bounding box in the processed image data;

send the present trajectories and the initialized trajectories to a user interface module; and display the trajectories at a display using the user interface module;

for every image not the first or $[(n+1)\times i]^{th}$ image:

calculate camera motion compensation for the image data received as compared to the image data of the immediate previous image;

predict the next parameters of the bounding box of each of the at least one tool using a Kalman filter and the calculated camera motion compensation;

send the predicted image data to the user interface; and display the predicted image at a display using the user interface module, wherein n is a predetermined integer and i starts at 1 and increases by 1 each time, wherein the processed image data comprises a location and a size of the bounding box, a label, and the bounding box confidence, wherein the parameters of the bounding box comprise a location, a size, a velocity, and a velocity of size change of the bounding box, and wherein the trajectory is a collection of digital image data concerning a bounding box collected over time.

13. The system of claim 12, wherein the instructions, when executed, further causes the processor to:

generate a first input feature vector based on the image data; and apply the first input feature vector to the first trained neural network model to generate a first output feature vector, wherein the first output feature vector indicates the location for the bounding box around each of the at least one tool.

14. The system of claim 12, wherein the instructions, when executed, further causes the processor to apply the processed image data to the second trained neural network model, wherein applying the processed image data to the second trained neural network model comprises:

generating a second input feature vector based on the processed image data; and applying the second input feature vector to the second trained neural network model to generate a second output feature vector, wherein the second output feature vector indicates the location for the distal end of each of the at least one tool.

15. The system of claim 12, wherein calculating camera motion compensation comprises using Oriented FAST Rotated BRIEF technique or sparse optical flow technique.

16. The system of claim 12, wherein updating the Kalman filter comprises updating the location, label, and size of the bounding box and updating estimated current state variables using weighted averages.

17. The system of claim 12, wherein the value of n is chosen by a user.

18. The system of claim 12, wherein n is 0.

19. The system of claim 12, wherein the instructions, when executed, further causes the processor to, prior to applying the image data to the first trained neural network model:

receive a plurality of reference image data of a reference surgical video, wherein each reference image data represents a respective image frame showing a plurality of tools;

generate, for each of the plurality of reference image data, a reference input feature vector indicating relevant features of the reference image data, and a reference output feature vector indicating a location for a bounding box around each of the plurality of tools; and train, by associating each reference input feature vector with its respective reference output feature vector, a neural network to form the first trained neural network model.

20. The system of claim 12, wherein the instructions, when executed, further causes the processor to:

set a value reflecting how many times a trajectory is marked as lost before removing a trajectory;

count the times a trajectory is marked as lost; and remove the trajectory when the times have reached the value, wherein the value is an integer.

* * * * *